US011365386B2

(12) United States Patent
Gosselin et al.

(10) Patent No.: US 11,365,386 B2
(45) Date of Patent: Jun. 21, 2022

(54) CELLULAR BEHAVIOUR MONITORING DEVICE AND METHOD FOR MONITORING CHANGES IN CELLULAR BEHAVIOUR

(71) Applicant: UNIVERSITÉ LAVAL, Québec (CA)

(72) Inventors: Benoit Gosselin, Lac Beauport (CA); Younès Messaddeq, Quebec (CA); Jacques Corbeil, Saint-Augustin de Desmaures (CA); Eric Bharucha, St-Augustin-de-desmaures (CA)

(73) Assignee: UNIVERSITÉ LAVAL, Quebec (CA)

( * ) Notice: Subject to any disclaimer, the term of this patent is extended or adjusted under 35 U.S.C. 154(b) by 387 days.

(21) Appl. No.: 16/402,277

(22) Filed: May 3, 2019

(65) Prior Publication Data

US 2020/0347340 A1 Nov. 5, 2020

(51) Int. Cl.
*C12M 1/34* (2006.01)
*C12M 1/12* (2006.01)
(Continued)

(52) U.S. Cl.
CPC ............ *C12M 41/46* (2013.01); *C12M 23/12* (2013.01); *C12M 25/04* (2013.01); *C12M 29/04* (2013.01);
(Continued)

(58) Field of Classification Search
CPC ...... C12M 41/46; C12M 29/04; C12M 25/04; C12M 23/12; C12Q 1/02; B01L 3/50853;
(Continued)

(56) References Cited

U.S. PATENT DOCUMENTS 4,072,578 A 2/1978 Cady et al.
4,485,171 A 11/1984 Ikeda et al.
(Continued)

FOREIGN PATENT DOCUMENTS

| CN | 102213687 A | 10/2011 |
| EP | 1473359 A1 | 3/2004 |
| WO | 2011045547 A1 | 4/2011 |

OTHER PUBLICATIONS

Nichols, D., et al. "Use of ichip for high-throughput in situ cultivation of "uncultivable" microbial species" Appl. Environ. Microbiol. 76.8 (2010): 2445-2450.
(Continued)

*Primary Examiner* — Michael L Hobbs
(74) *Attorney, Agent, or Firm* — Alexandre Daoust; Norton Rose Fulbright Canada LLP

(57) ABSTRACT

There is described a cellular behaviour monitoring device for monitoring changes in behaviour of cells contained in a sample. The device generally has a well plate with a sample receiving well recessed therein. A filter membrane extends across the well plate and hermetically covers the sample receiving well. The filter membrane has nutrient-permeable and cell-impermeable pores extending through the filter membrane. The device has an electrode layer extending across the filter membrane. The electrode layer has a substrate and behaviour monitoring electrodes spaced-apart from one another in a region of the substrate, with the region being aligned with the sample receiving well. The electrode layer has nutrient-permeable apertures distributed across the region, with at least some of pores are aligned with at least some of the apertures to allow fluid communication therebetween, and nutrient exchange between the sample receiving well and a surrounding environment.

17 Claims, 13 Drawing Sheets

(51) Int. Cl.
    C12Q 1/02        (2006.01)
    G01N 27/02       (2006.01)
    C12M 1/32        (2006.01)
    C12M 1/00        (2006.01)
    B01L 3/00        (2006.01)
(52) U.S. Cl.
    CPC .............. *C12Q 1/02* (2013.01); *G01N 27/026* (2013.01); *B01L 3/50853* (2013.01); *B01L 2300/0645* (2013.01); *B01L 2300/0681* (2013.01); *B01L 2300/0829* (2013.01)
(58) Field of Classification Search
    CPC ..... B01L 2300/0681; B01L 2300/0645; B01L 2300/0829; G01N 27/026
    See application file for complete search history.

(56) References Cited

U.S. PATENT DOCUMENTS

| | | | |
|---|---|---|---|
| 5,353,802 | A | 10/1994 | Ollmar |
| 6,596,532 | B1 | 7/2003 | Hyman et al. |
| 7,011,957 | B2 | 3/2006 | Lewis et al. |
| 7,560,269 | B2 | 7/2009 | Wang et al. |
| 8,936,191 | B2 | 1/2015 | Potyrailo et al. |
| 2002/0197709 | A1 | 12/2002 | Van der Weide et al. |
| 2004/0152067 | A1* | 8/2004 | Wang ............... G01N 33/54366 435/4 |
| 2005/0142033 | A1* | 6/2005 | Glezer ................... G01N 21/66 422/400 |
| 2007/0090926 | A1 | 4/2007 | Potyrailo et al. |
| 2009/0278685 | A1 | 11/2009 | Potyrailo et al. |
| 2014/0268523 | A1 | 9/2014 | Gogoi |
| 2017/0046610 | A1 | 2/2017 | Novoselov et al. |
| 2018/0080891 | A1 | 3/2018 | Potyrailo et al. |

OTHER PUBLICATIONS

Sylvain, Matthieu, et al. "The EcoChip: A wireless multi-sensor platform for comprehensive environmental monitoring." IEEE transactions on biomedical circuits and systems 12.6 (2018): 1289-1300.
Courbat, J., et al. "Multi sensor platform on plastic foil for environmental monitoring" Procedia Chemistry 1.1 (2009): 597-600.
Fourie, Coenrad J., P. J. Van Der Westhuyzen, and P. C. Van Niekerk. "An automated system for impedance measurements in milk." AFRICON 2007. IEEE, 2007.
Ghaffari, Seyed, et al. "A wireless multi-sensor dielectric impedance spectroscopy platform." Sensors 15.9 (2015): 23572-23588.
Grossi, Marco, et al. "Bacterial concentration detection using a portable embedded sensor system for environmental monitoring." 2017 7th IEEE International Workshop on Advances in Sensors and Interfaces (IWASI). IEEE, 2017.
Jang, Am, et al. "State-of-the-art lab chip sensors for environmental water monitoring." Measurement Science and Technology 22.3 (2011): 032001.
Kwasny, Dorota, et al. "Direct detection of candida albicans with a membrane based electrochemical impedance spectroscopy sensor." Sensors 18.7 (2018): 2214.
Montero-Rodriguez, J. J., et al. "Development of an impedance spectroscopy device for on-line cell growth monitoring." Electronics Letters 53.15 (2017): 1025-1027.
Paredes, J., et al. "Interdigitated microelectrode biosensor for bacterial biofilm growth monitoring by impedance spectroscopy technique in 96-well microtiter plates." Sensors and Actuators B: Chemical 178 (2013): 663-670.
Peršoh, Derek, Alfons R. Weig, and Gerhard Rambold. "A transcriptome—targeting EcoChip for assessing functional mycodiversity." Microarrays 1.1 (2011): 25-41.
Sousa, Pedro José, et al. "NSensor—Wireless Sensor Network for Environmental Monitoring." International Journal of Interactive Mobile Technologies (iJIM) 11.5 (2017): 25-36.
Menon, KA Unnikrishna, P. Divya, and Maneesha V. Ramesh. "Wireless sensor network for river water quality monitoring in India." 2012 Third International Conference on Computing, Communication and Networking Technologies (ICCCNT'12). IEEE, 2012.
Wu, Chun-Chang, et al. "A self-sustained wireless multi-sensor platform integrated with printable organic sensors for indoor environmental monitoring." Sensors 17.4 (2017): 715.
Alliedmarketresearch (2015). "Cheese Market by Source (Cow Milk, Sheep Milk, Goat Milk, and Buffalo Milk)" https://www.alliedmarketresearch.com/cheese-market.
BCG (2008) "archives d'entreprises" https://archives.entreprises.gouv.fr/2012/www.industrie.gouv.fr/eco.industries/ccles/depollution.pdf.
Dufresne (2013). "les technologies de traitement des sols contaminés : lesquelles sont durables ?". Mémoire de M, Env, Université de Sherbrooke. https://savoirs.usherbrooke.ca/bitstream/handle/11143/7176/cufe_Dufresne_Myriam_essai357.df?sequence=1 &is Allowed=y.
ECCC (2015). "Federal contaminated sites action plan (FCSAP)". http://publications.gc.ca/collections/collection_2018/eccc/En1-43-2016-eng.pdf.
MDDEFP (2013). "bilan sur la gestion des terrains contaminés". http://www.mddelcc.gouv.qc.ca/sol/terrains/bilan/bilan2010.pdf.
Ling, Losee L., et al. "A new antibiotic kills pathogens without detectable resistance." Nature 517.7535 (2015): 455.

* cited by examiner

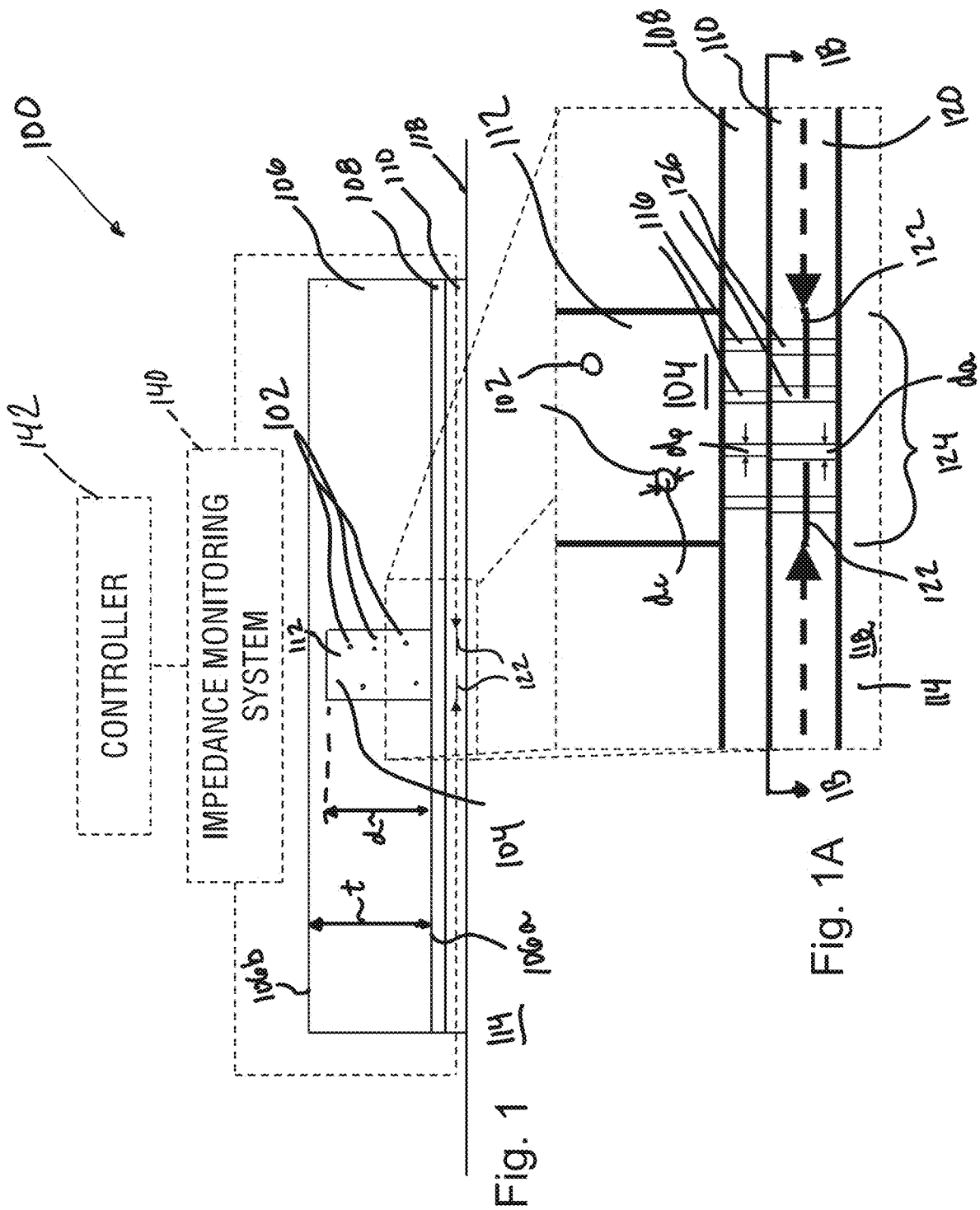

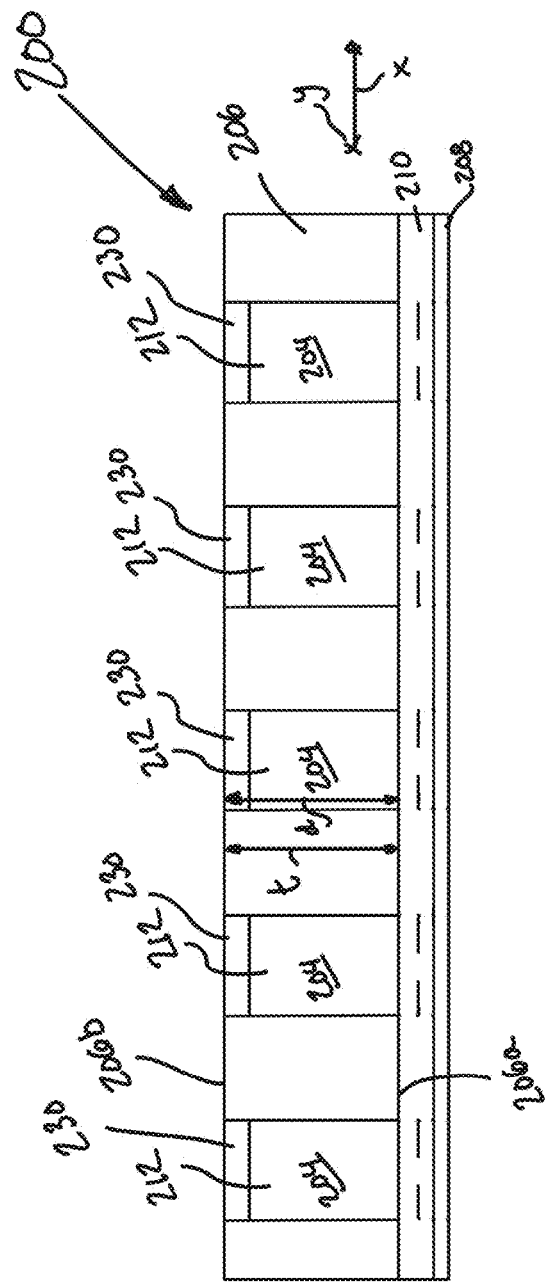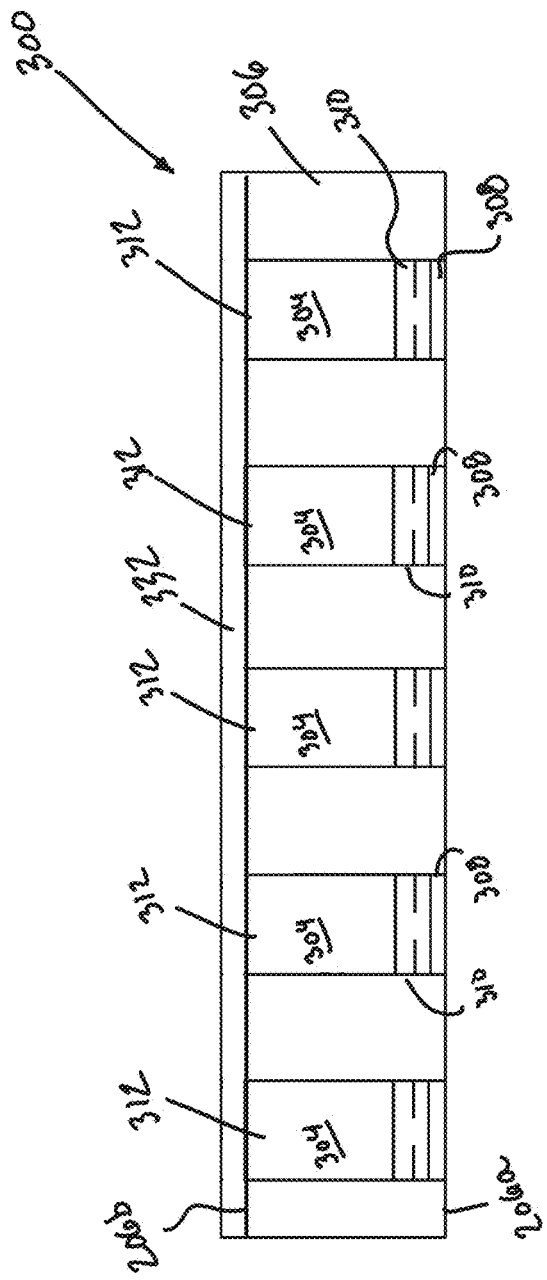

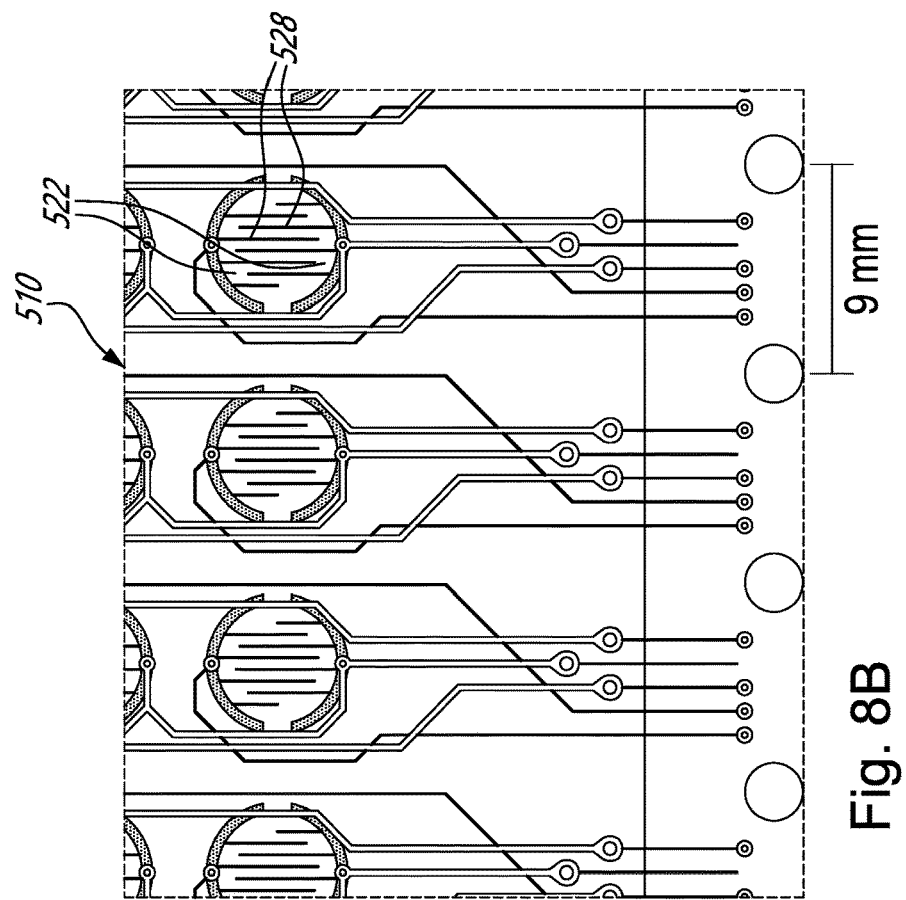
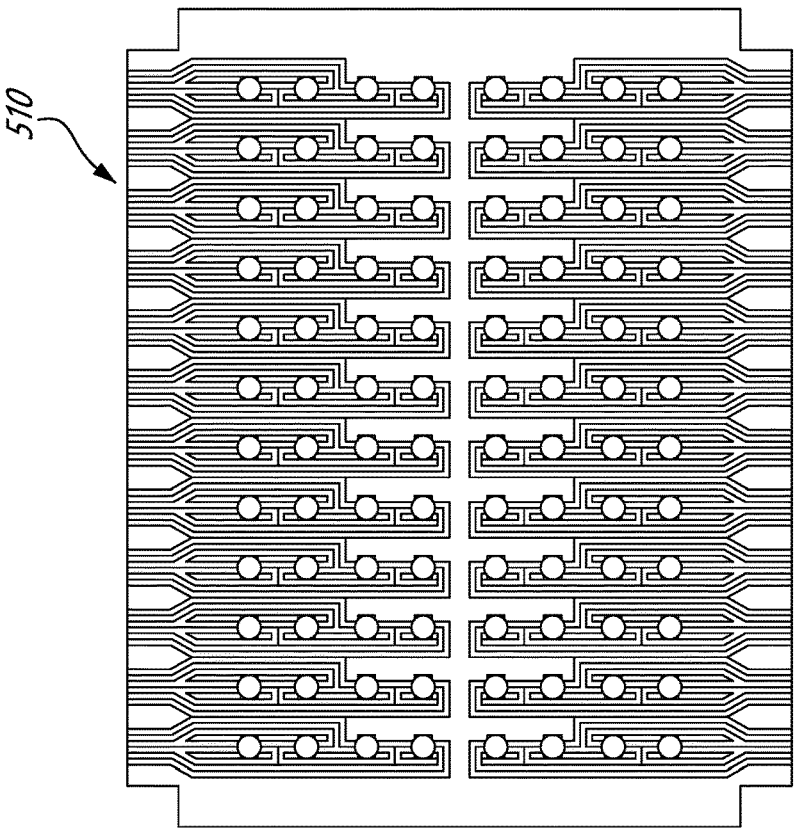

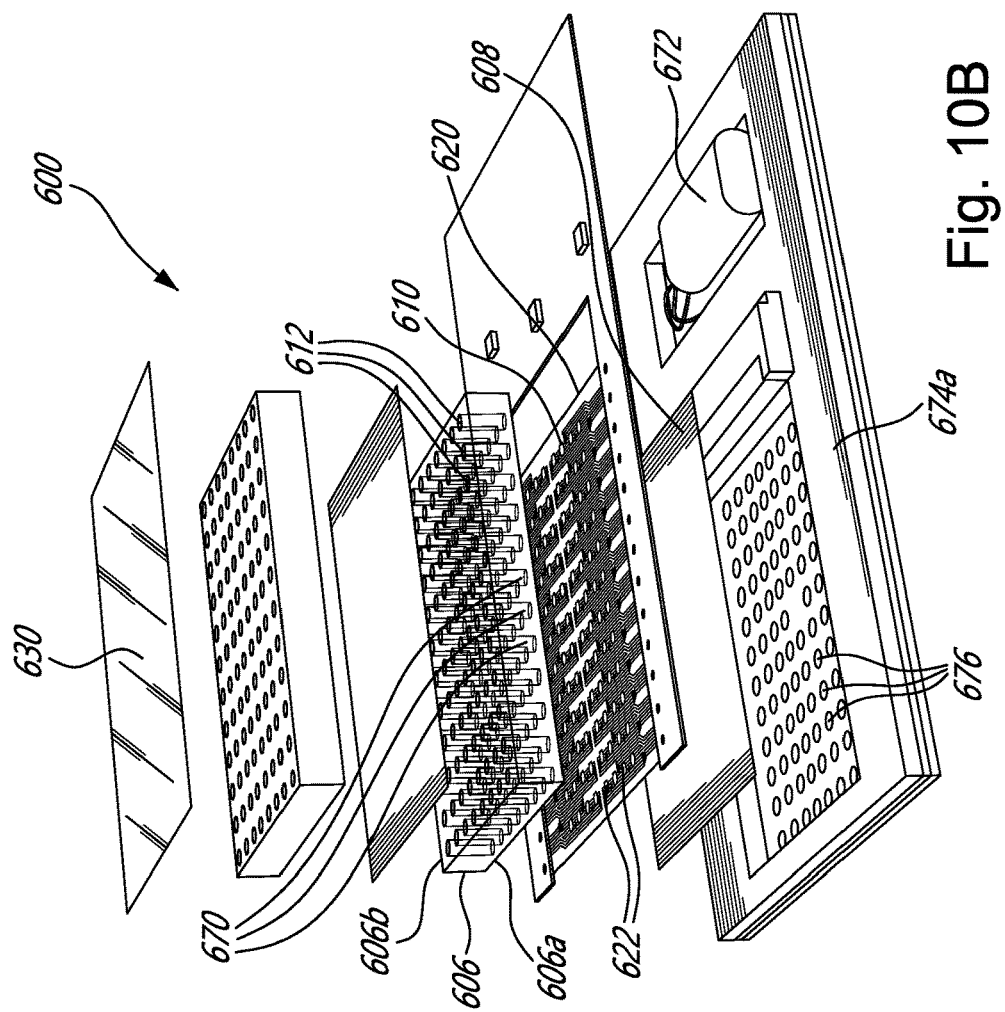
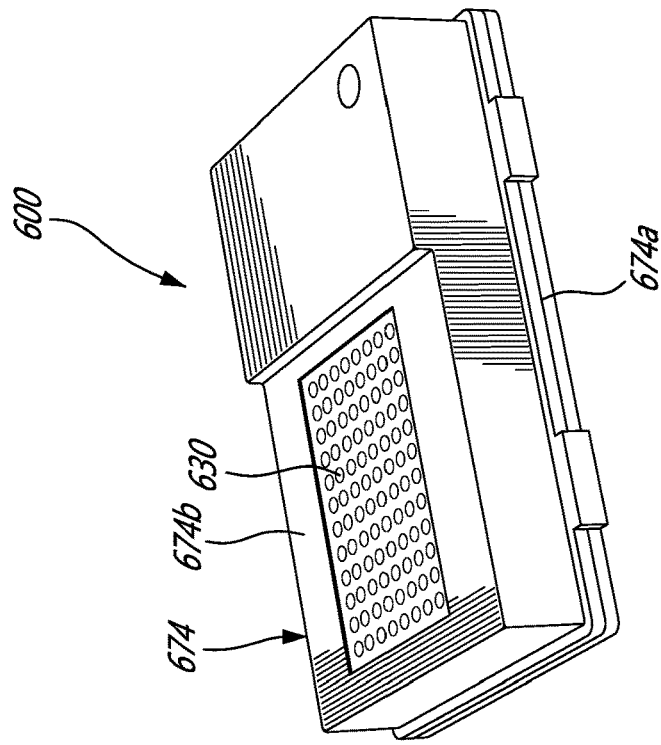
Fig. 10B
Fig. 10A

CELLULAR BEHAVIOUR MONITORING DEVICE AND METHOD FOR MONITORING CHANGES IN CELLULAR BEHAVIOUR

FIELD

The improvements generally relate to cellular behaviour monitoring devices and more particularly to such devices which involve impedance monitoring.

BACKGROUND

U.S. Pat. No. 7,560,269 B2, to Wang et al., describes cell-substrate impedance monitoring devices that comprise electrode arrays on a non-conducting substrate, in which each of the arrays has an approximately uniform electrode resistance across the entire array. Each cell-substrate monitoring device comprises multiple chambers each having an electrode array, an impedance analyser, a device station that connects arrays of individual wells to the impedance analyzer, and software for controlling the device station and impedance analyzer.

Although existing cell-substrate impedance monitoring devices have been satisfactory to a certain degree, there remains room for improvement, especially in providing such monitoring devices which can interact with a surrounding environment.

SUMMARY

In an aspect, there is described a cellular behaviour monitoring device for monitoring changes in behaviour of cells contained in a sample. It is intended that monitoring cellular behaviour can include the monitoring of, but not limited to, cellular growth, cellular growth stagnation and/or cellular death pertaining to the sample. The cellular behaviour monitoring device has a well plate, a filter membrane and an electrode layer mounted to one another. More specifically, the well plate has a first surface, a second surface opposite the first surface, and at least one sample receiving well recessed from the first surface of the well plate. In some embodiments, at least one sample receiving well includes a plurality of sample receiving wells spaced-apart from one another on the well plate. The filter membrane extends across the first surface of the well plate and hermetically covers the sample receiving well(s). The filter membrane has pores extending through the filter membrane. The pores have a dimension such that they are cell-impermeable while being nutrient-permeable. In other words, the dimension of the pores exceeds a pore dimension generally associated to nutrients that can feed the cells while the dimension of the pores can be smaller than a cell dimension generally associated to the cells. Accordingly, the pores can allow nutrient exchange but not cellular exchange with a surrounding environment. To monitor any change in behaviour of the cells, the electrode layer extends across the well plate, too. More specifically, the electrode layer has behaviour monitoring electrodes spaced-apart from one another in one (or more) region(s) of the electrode layer which is(are) aligned with the sample receiving well(s). The electrode layer has apertures distributed across the region(s). It is encompassed that the apertures of the electrode layer have a dimension exceeding the dimension of the pores of the filter plate. With at least some of the pores being aligned with at least some of the apertures, fluid communication is allowed between the sample receiving well(s) and the surrounding environment, thereby allowing the cells of the sample to be fed by nutrients provided by the surrounding environment while preventing them from leaving the sample receiving well(s).

In accordance with an aspect, there is provided a cellular behaviour monitoring device for monitoring changes in behaviour of cells contained in a sample, the cellular behaviour monitoring device comprising: a well plate having a first surface, a second surface opposite to the first surface, and at least one sample receiving well recessed from the first surface of the well plate; a filter membrane extending across the first surface of the well plate and hermetically covering the at least one sample receiving well, the filter membrane having a plurality of pores extending through the filter membrane, the plurality of pores having a dimension exceeding a nutrient dimension and being smaller than a cell dimension; and an electrode layer extending across the filter membrane, the electrode layer having a substrate and a plurality of behaviour monitoring electrodes spaced-apart from one another in a region of the substrate, the region being aligned with the at least one sample receiving well, the electrode layer having a plurality of apertures distributed across the region, the plurality of apertures having a dimension exceeding the dimension of the plurality of pores, at least some of the plurality of pores being aligned with at least some of the plurality of apertures to allow fluid communication therebetween.

In accordance with another aspect, there is provided a method for monitoring changes in behaviour of a plurality of cell samples received in a plurality of sample receiving wells using a cellular behaviour monitoring device, the method comprising: hermetically covering the plurality of sample receiving wells with a filter membrane having a plurality of nutrient-permeable and cell-impermeable pores and with an electrode layer having a plurality of behaviour monitoring electrodes extending across said plurality of sample receiving wells, the electrode layer having at least some apertures aligned with at least some of the nutrient-permeable and cell-impermeable pores of the filter membrane to allow fluid communication therebetween; and the plurality of cell samples exchanging nutrients with a surrounding environment through the nutrient-permeable and cell-impermeable pores of the filter membrane and through the apertures of the electrode layer.

Many further features and combinations thereof concerning the present improvements will appear to those skilled in the art following a reading of the instant disclosure.

DESCRIPTION OF THE FIGURES

In the figures,

FIG. 1 is a schematic view of an example of a cellular behaviour monitoring device, shown with an impedance monitoring system and a controller, in accordance with one or more embodiments;

FIG. 1A is an enlarged view of a portion of the cellular behaviour monitoring device of FIG. 1;

FIG. 2 is a sectional view of another example of a cellular behaviour monitoring device, with an electrode layer extending across a well plate and a filter membrane extending across the electrode layer, in accordance with one or more embodiments;

FIG. 3 is a sectional view of another example of a cellular behaviour monitoring device, with individual electrode layers and individual filter membranes, in accordance with one or more embodiments;

FIG. 5B is a sectional view of the cellular behaviour monitoring device, taken along line 5B-5B of FIG. 5, in accordance with one or more embodiments;

FIG. 8A is a top plan view of an example of an electrode layer of the cellular behaviour monitoring device of FIG. 5, in accordance with one or more embodiments;

FIG. 8B is an enlarged view of an example of an electrode layer of the cellular behaviour monitoring device of FIG. 5;

FIG. 10A is an oblique view of another example of another example of cellular behaviour monitoring device, shown with growth medium, in accordance with one or more embodiments;

FIG. 10B is an exploded view of the cellular behaviour monitoring device of FIG. 10A.

DETAILED DESCRIPTION

Figure 1B:
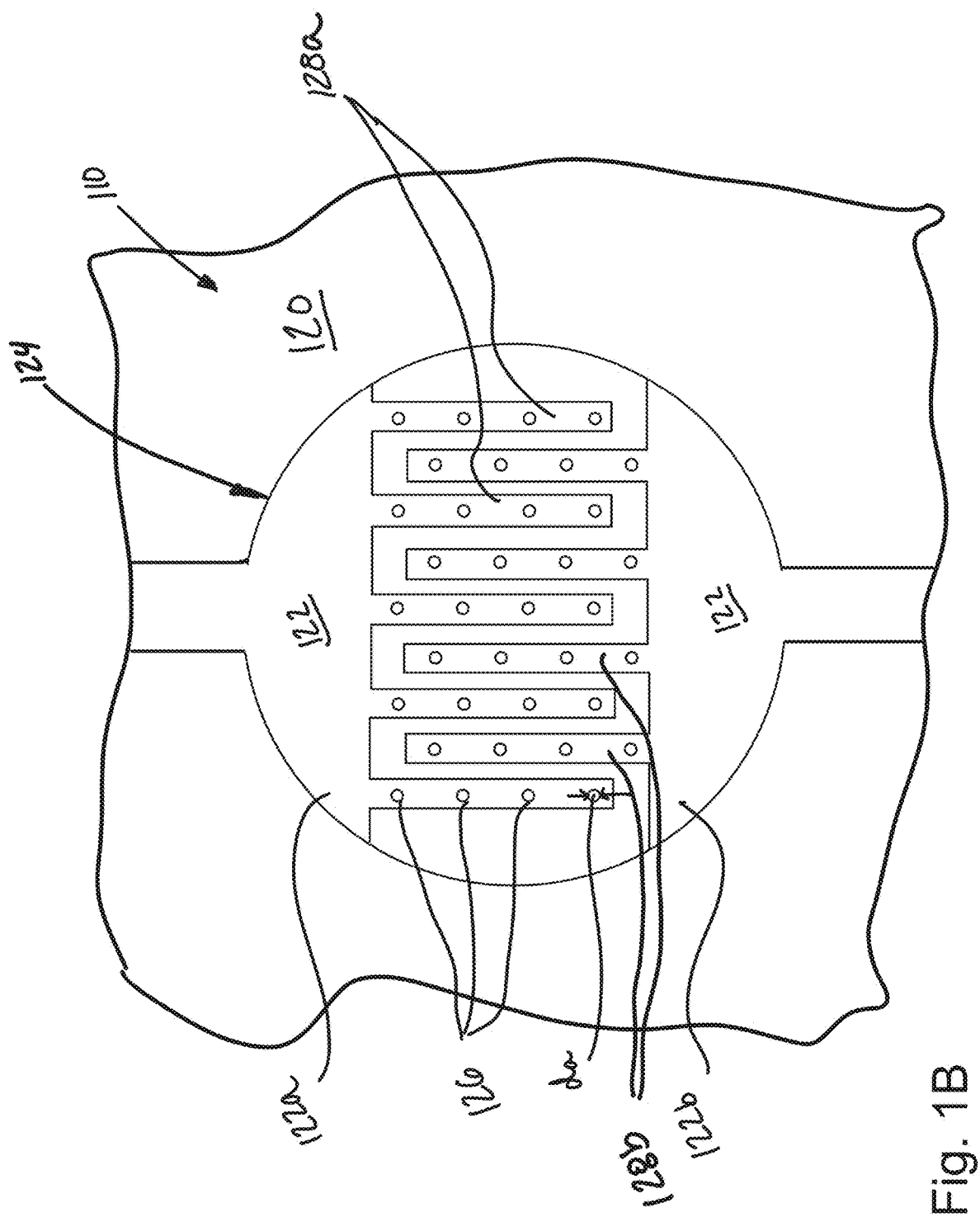
FIG. 1B is a top view of a region of the cellular behaviour monitoring device of FIG. 1 taken along line 1B-1B of FIG. 1.

FIG. 1 shows an example of a cellular behaviour monitoring device 100 for monitoring changes in behaviour of cells 102 (e.g., microorganisms, bacteria and the like) contained in a sample 104. For instance, the sample 104 can be provided in the form of a given amount of soil diluted in water. In some embodiments, the sample 104 can be a 1 million fold dilution of soil into water. As shown, the cellular behaviour monitoring device 100 has a well plate 106 to which are mounted a filter membrane 108 and an electrode layer 110.

The well plate 106 has a first surface 106a, a second surface 106b which is opposite to the first surface 106a, and one or more sample receiving well(s) (hereinafter "the sample receiving well 112") recessed from the first surface 106a of the well plate 106. The sample receiving well 112 is referred to as such as it is sized and shape for receiving any type of sample 104 containing cells 102. The volume of the sample receiving well 112 can different from embodiment to another. For instance, the volume of the sample receiving well 112 can generally range between about 0.1 mL and about 0.25 mL, and most preferably between about 0.1 mL and about 0.2 mL. However, these volumes can differ depending on the embodiment.

As shown in this example, the sample receiving well 112 is recessed only partially through the well plate 106. In other words, the sample receiving well 112 is recessed from a given depth d which is lower than a thickness t of the well plate 106. However, in some other embodiments, the sample receiving well 112 can be fully recessed through the well plate 106, from the first surface 106a up to the second surface 106b, as will be discussed below.

Still referring to FIG. 1, the filter membrane 108 extends across the first surface 106a of the well plate 106 in a manner which hermetically covers the sample receiving well 112. Accordingly, if not for pores of the filter membrane 108, the sample 104 received inside the sample receiving well 112 would be isolated from a surrounding environment 114. However, as can be expected, the filter membrane 108 has pores 116 extending through the filter membrane 108, such as shown in FIG. 1A. The pores 116 have a dimension $d_p$ exceeding a nutrient dimension $d_n$ ($d_p > d_n$) and being smaller than a cell dimension $d_c$ ($d_p < d_c$). As such, the pores 116 are nutrient-permeable while being cell-impermeable to allow the cells 102 of the sample 104 received in the sample receiving well 112 to exchange with the surrounding environment 114. For instance, nutrients stemming from ground 118 can pass through the filter membrane 108 via the pores 116 so as to feed the cells 104 in at least some circumstances. In some embodiments, the dimension $d_p$ of the pore 116 can generally range between about 0.1 µm and about 0.25 µm, and preferably between about 0.1 µm and about 0.2 µm. However, these dimensions can differ depending on the embodiment.

As shown in the illustrated example, the electrode layer 110 extends across the filter membrane 108. In this embodiment, the filter membrane 108 is sandwiched between the well plate 106 and the electrode layer 110. However, in some other embodiments, the electrode layer 110 can be sandwiched between the well plate 106 and the filter membrane 108 as will be discussed below. As such, which one of the filter membrane 108 and the electrode layer 108 is directly received on the first surface 106a of the well plate 106 can differ depending on the embodiment.

As best shown in FIG. 1A, the electrode layer 110 has a substrate 120 which is made of an electrically insulating material and behaviour monitoring electrodes 122 which are spaced-apart from one another in a region 124 of the substrate 120. As shown, the region 124 is aligned with the sample receiving well 112. The electrode layer 110 has apertures 126 distributed across the region 124, where the apertures 126 have a dimension $d_a$ which exceeds at least the dimension $d_p$ of the pores 116 ($d_a > d_r$). It is intended that at least some of the pores 116 are aligned with at least some of the apertures 126 in order to allow fluid communication between the sample receiving well 112 and the surrounding environment 114. In some embodiments, the dimension $d_a$ of the apertures can generally range between about 100 µm and about 200 µm. However, these dimensions can differ depending on the embodiment.

As shown in this example. the behaviour monitoring electrodes 122 extend in a parallel manner relative to the well plate 106, the filter membrane 108 and/or the electrode layer 110. However, in some other embodiments, the behaviour monitoring electrodes 122 may not extend parallel to the electrode layer 110, as they can run across thereto in the form of through via, for instance.

FIG. 1B shows a top view encompassing the region 124 of the electrode layer 110. As shown, the behaviour monitoring electrodes 122 have at least a ground electrode 122a and a well electrode 122b which are opposite to one another and electrically insulated from one another. As illustrated in this specific embodiment, the well electrode 122b has monitoring fingers 128a extending across the region 124 towards the ground electrode 122a whereas the ground electrode 122a has monitoring fingers 128b extending across the region 124 towards the well electrode 122b. In this example, it was found convenient to provide the monitoring fingers 128b of the well electrodes 122b so that they be spaced-apart and also interspersed with the monitoring fingers 128a of the ground electrode 122a.

In this specific embodiment, it was found convenient to provide the apertures 126 of the electrode layer 110 directly through the behaviour monitoring electrodes 122. More specifically, in this example, the apertures 126 are provided through the monitoring fingers 128a and/or 128b. However, in some other embodiments, it can be preferred to space the apertures 126 from the behaviour monitoring electrodes 122. In such embodiments, the apertures 126 are provided away from the behaviour monitoring electrodes 122, directly through the substrate 110, an example of which will be described below.

In this embodiment, the region 124 within which the electrodes are provided is circular to fit a circular end of the cylindrical shape of the sample receiving well 112. Although the shape of the sample receiving well 112 has a cylindrical shape extending perpendicularly to the well plate 106 in this embodiment, the shape of the sample receiving well 112 can differ from one embodiment to another. For instance, the sample receiving well 112 have a rectangular prism shape or any suitable type of shape, in which case the shape of the region 124 may so follow.

FIG. 2 shows another example of a cellular behaviour monitoring device 200. In this example, the cellular behaviour monitoring device 200 has a well plate 206 with first and second opposite surfaces 206a and 206b, and a plurality of sample receiving wells 212 recessed from the first surface 206a of the well plate 206.

As shown, the sample receiving wells 212 are spaced-apart from one another across the well plate 206. The sample receiving wells 212 can be spaced-apart from one another to form an array of sample receiving wells 212. The array can have any suitable shape. One example array can be rectangular, in which there are a number X of sample receiving wells 212 along the x-axis and a number Y of sample receiving wells 212 along the y-axis, with both X and Y being positive integers. The number of sample receiving wells 212 can differ from an embodiment to another. However, in some embodiments, it was found convenient to provide four sample receiving wells 212, twelve sample receiving wells 212, 16 sample receiving wells 212, 96 sample receiving wells 212 or any other suitable number.

In this specific example, the sample receiving wells 212 extend through the well plate 206, from the first surface 206a up to the second surface 206b. In other words, the sample receiving wells 212 are fully recessed across the well plate 206 (d=t). Accordingly, windows 230 are provided to each of the sample receiving wells 212. More specifically, in the illustrated embodiment, the windows 230 are coplanar with the second surface 206b of the well plate 206 and hermetically cover each one of the sample receiving wells 212. In some other embodiments, the windows 230 are optically transparent to sunlight, thereby allowing sunlight to reach the samples 204. As can be understood, the windows 230 need not be optically transparent. Each window 230 can be removably mounted to the well plate 206. For instance, the windows 230 can be pressure-fitted within a periphery of the sample receiving wells 212.

Also in this embodiment, the electrode layer 210 is sandwiched between the well plate 206 and the filter membrane 208 as will be discussed below. As such, the electrode layer 210 is directly received on the first surface 206a of the well plate 206.

FIG. 3 shows another example of a cellular behaviour monitoring device 300. In this embodiment, the cellular behaviour monitoring device 300 has a well plate 306 with first and second opposite surfaces 306a and 306b, and a plurality of sample receiving wells 312 recessed from the first surface 306a of the well plate 306.

In this embodiment, the cellular behaviour monitoring device 300 has a lid mounted on the second surface 306b to extend across the sample receiving wells 312 in an hermetic manner. In some embodiments, the lid 332 can be partially or wholly optically transparent to sunlight, thereby allowing sunlight to pass through the lid 332, or through at least one of its optically transparent portion, to reach the samples 304 received in the sample receiving wells 312. The lid 332 can be removably mounted to the well plate 306 so as to ease access to the sample receiving wells 312, in some embodiments.

In this specific example, each sample receiving well 312 has its own individual electrode layer 310 and its own individual filter membrane 308. extend through the well plate 206, from the first surface 206a up to the second surface 206b. The individual electrode layers 310 and the individual filter membranes 308 can be removably mounted to the sample receiving wells 312 in a manner which hermetically seals the sample receiving wells 312. For instance, the individual electrode and filter membranes 310 and 308 can be pressure-fitted within a periphery of the sample receiving wells 312.

Referring back to FIG. 1, an impedance monitoring system 140 is connected to the behaviour monitoring electrodes 122. In this specific embodiment, the impedance monitoring system 140 measures impedance values $I_i$ indicative of impedance I between the behaviour monitoring electrodes 122 over time, with i being a positive integer. Accordingly, any change in the behaviour of the sample 104 containing the cell 102 received within the sample receiving well 112 may change the impedance I that is experienced between the behaviour monitoring electrodes 122. Examples of the impedance monitoring system 140 are described below.

A controller 142 can also be provided to, when communicatively coupled to the impedance monitoring system 140, generate a signal based on the measured impedance values $I_i$. For instance, the controller 142 can be configured to determine a growth rate indicative of growth of the cells 102 of the sample 104 received in the sample receiving well 112. The controller 142 can also be configured to generate an alert or other information on the basis of the measured impedance values $I_i$.

The controller 142 can be provided as a combination of hardware and software components. The hardware components can be implemented in the form of a computing device 400, an example of which is described with reference to FIG. 4. Moreover, the software components of the controller 142 can be implemented in the form of a software application.

Figure 4:
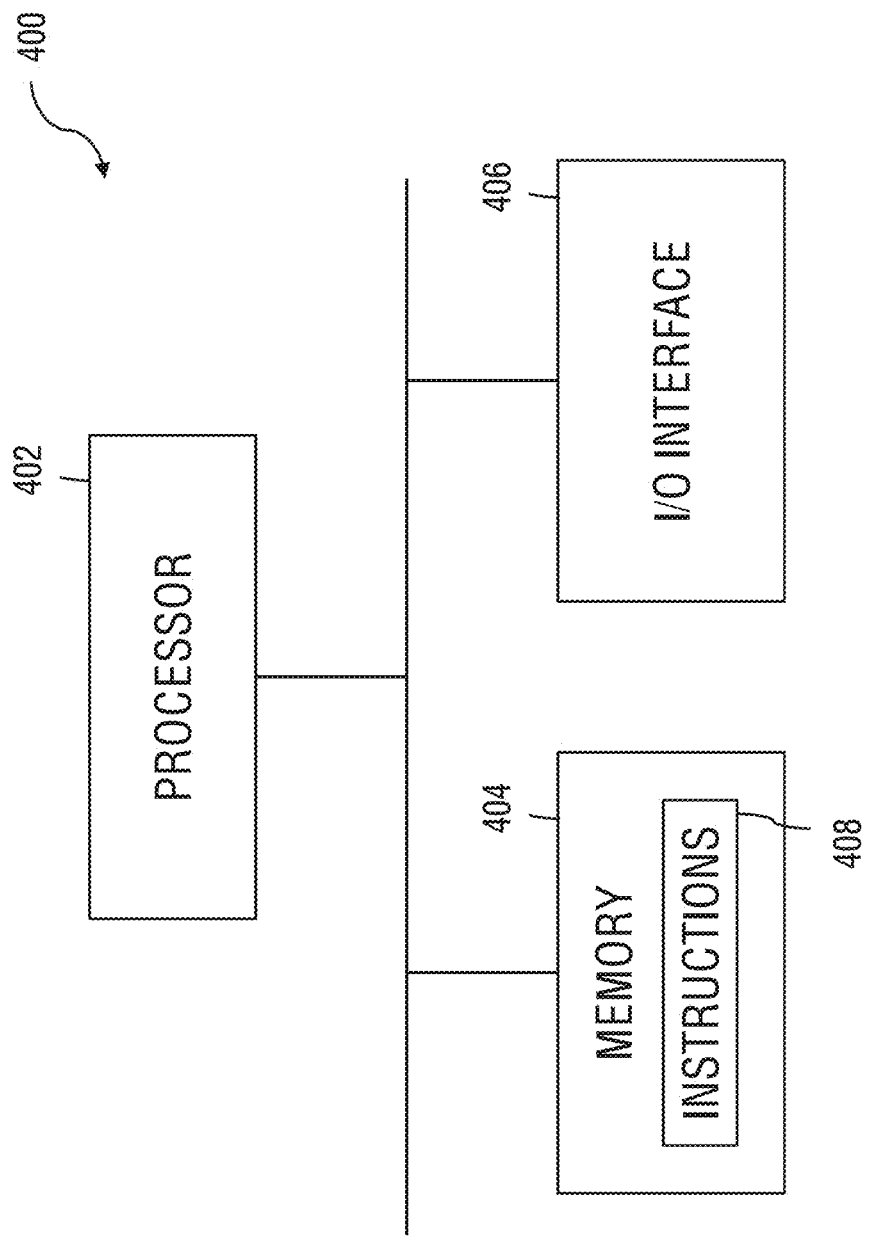
FIG. 4 is a schematic view of an example of a computing device of the controller of FIG. 1, in accordance with one or more embodiments.

Referring to FIG. 4, the computing device 400 can have a processor 402, a memory 404, and I/O interface 406. Instructions 408 for determining a growth rate, generating an alert and/or storing the measured impedance values $I_i$ can be stored on the memory 404 and accessible by the processor 402.

The processor 402 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 404 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 406 enables the computing device 400 to interconnect with one or more input devices, such as the impedance monitoring system 140, temperature sensor(s), luminosity sensor(s), humidity sensor(s), pH sensor(s), $CO_2$ sensor(s) and the like, or with one or more output devices such as a remote network or base (e.g., located at about 50 m or more), a display and the like.

Each I/O interface 406 enables the controller 142 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. WMAX), SS7 signaling network, fixed line, local area network, wide area network, and others, including any combination of these.

The computing device 400 described above are meant to be examples only. Other suitable embodiments of the controller 142 can also be provided, as it will be apparent to the skilled reader.

Figure 5:
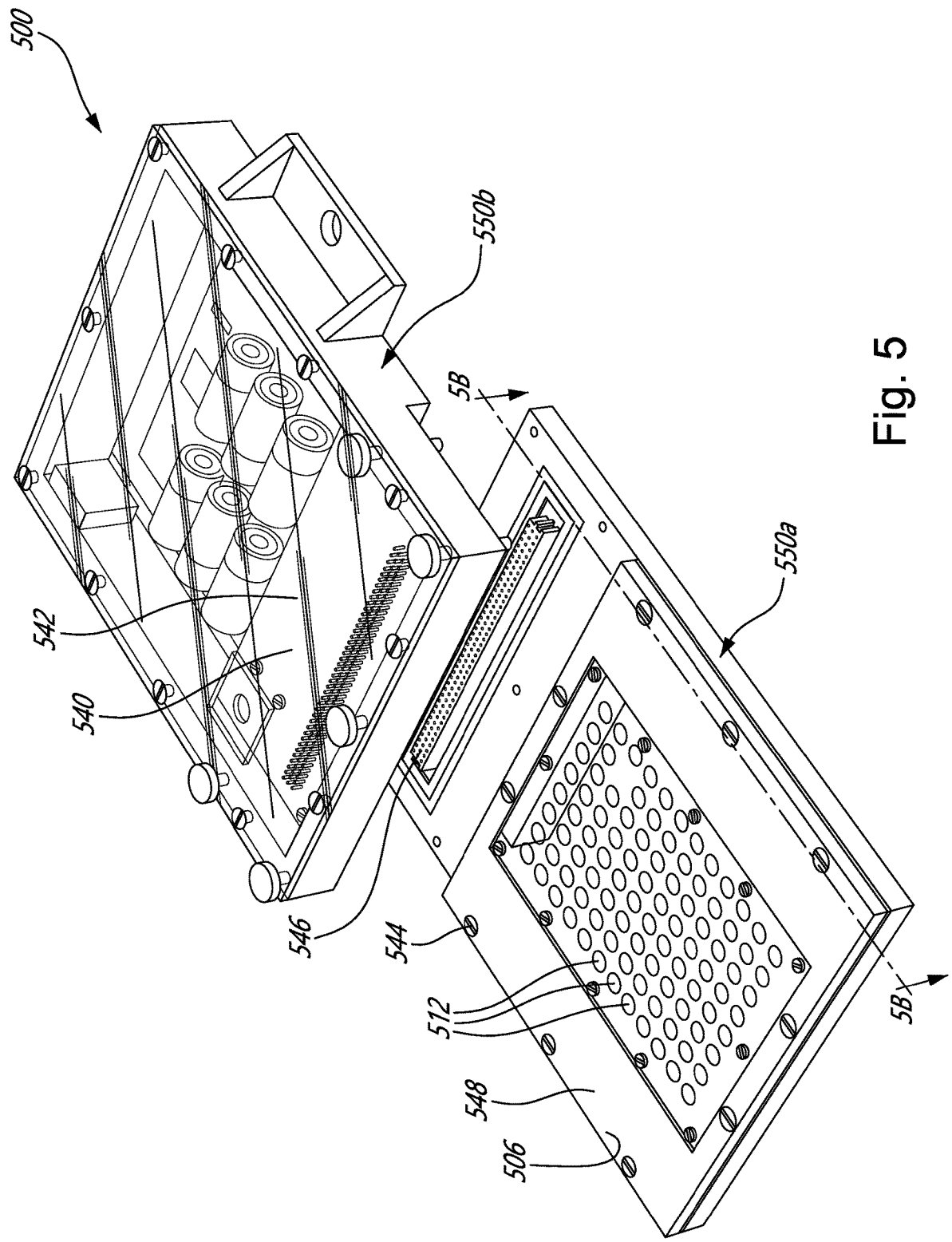
FIG. 5 is an oblique view of another example of cellular behaviour monitoring device, shown connected to an impedance monitoring system and a controller via an edge connector, in accordance with one or more embodiments.

Example 1—Cellular Behaviour Monitoring Device: a Wireless Multi-Sensor Platform for Comprehensive Environmental Monitoring Referring now to FIG. 5 and following, this example presents a new autonomous wireless cellular behaviour monitoring device 500 intended for the monitoring of microorganisms and molecules found in harsh environments, like in the northern climates. The cellular behaviour monitoring device 500 can include a layered multi-well plate 506 that allows changes in behaviour (e.g., growth, death) of single strain microorganisms, within a one or more sample receiving wells 512 of the well plate 506, isolated from environmental samples from Northern habitats. It can be deployed in the field for continuous monitoring of microbiological growth within 96 individual sample receiving wells 512 through a multichannel electro-chemical impedance monitoring circuit 540. It is envisaged that additional sensors can be provided for monitoring luminosity, humidity, temperature, pH, and $CO_2$ release. The controller, provided in the form of an embedded electronic board 542, is equipped with a flash memory to accumulate and store sensor data for long periods of time, as well as with a low-power micro-controller, and a power management unit to control and supply all electronic building blocks. When a receiver is located within the transmission range of the cellular behaviour monitoring device 500, a low power wireless transceiver allows transmission of sensor data stored from on-board memory. The results presented herein have been obtained in the field during a pilot study performed with the cellular behaviour monitoring device 500 deployed in the village of Kuujjuarapik, at a latitude of 55 degrees, in Northern Canada.

Climate changes and global warming receives lots of attentions each year, but measuring their various impacts on the environment remains a challenge. An effective way to evaluate these effects is to study the microorganisms that grow in those environments. However, these changes may not be notably visible in regions where the microbiome is not well known, like in Northern areas. One exemplary use of the cellular behaviour monitoring device 500 can be to monitor, comprehend and valorize microorganisms and molecules found in the North. One aim can be to identify sentinel microorganisms that are signposts of specific environmental changes across a gradient of Northern regions under the influence of global warming, human interventions and the presence of contaminants, and to identify unique molecules in these extreme environments that have potential usage in biological and industrial processes.

Since microorganisms are very difficult to cultivate, specialized isolation chambers enabling cultures in situ in diverse environments can be used. While such isolation chambers may allow the growth of microorganisms in natural environments, they may not allow the simultaneous environmental monitoring of the growing conditions. Having access to these conditions through growth rate measurement and environmental monitoring could lead to a better understanding of molecules and microorganisms found in the Northern regions.

This following presents another example of the cellular behaviour monitoring device 500 which allows the growth of single strain microorganism, within individual wells 512, isolated from environmental samples from Northern habitats, in the field. The cellular behaviour monitoring device 500 can measure the growth rate of microorganisms, and their environmental conditions in-situ in some embodiments, through the cellular behaviour monitoring device 500, to gain a better understanding of Northern areas and their microbiome.

FIG. 5 shows an oblique view of the cellular behaviour monitoring device 500. As shown in this specific example, the cellular behaviour monitoring device 500 is a modular device 550 including two distinct removable parts 550a and 550b. The cellular behaviour monitoring device 500 has the embedded electronic board 542 including different sensor interface circuits, including the impedance monitoring system 540, and a layered structure 544 including a microfabricated array of electrode and 96 sample receiving wells 512 recessed in the well plate 506 that allows the growth of single microorganisms isolated from diluted environmental samples from Northern habitats. As depicted, the embedded electronic board 542 and the layered structure 544 are connected together through an edge connector 546 in this example.

Figure 5A:
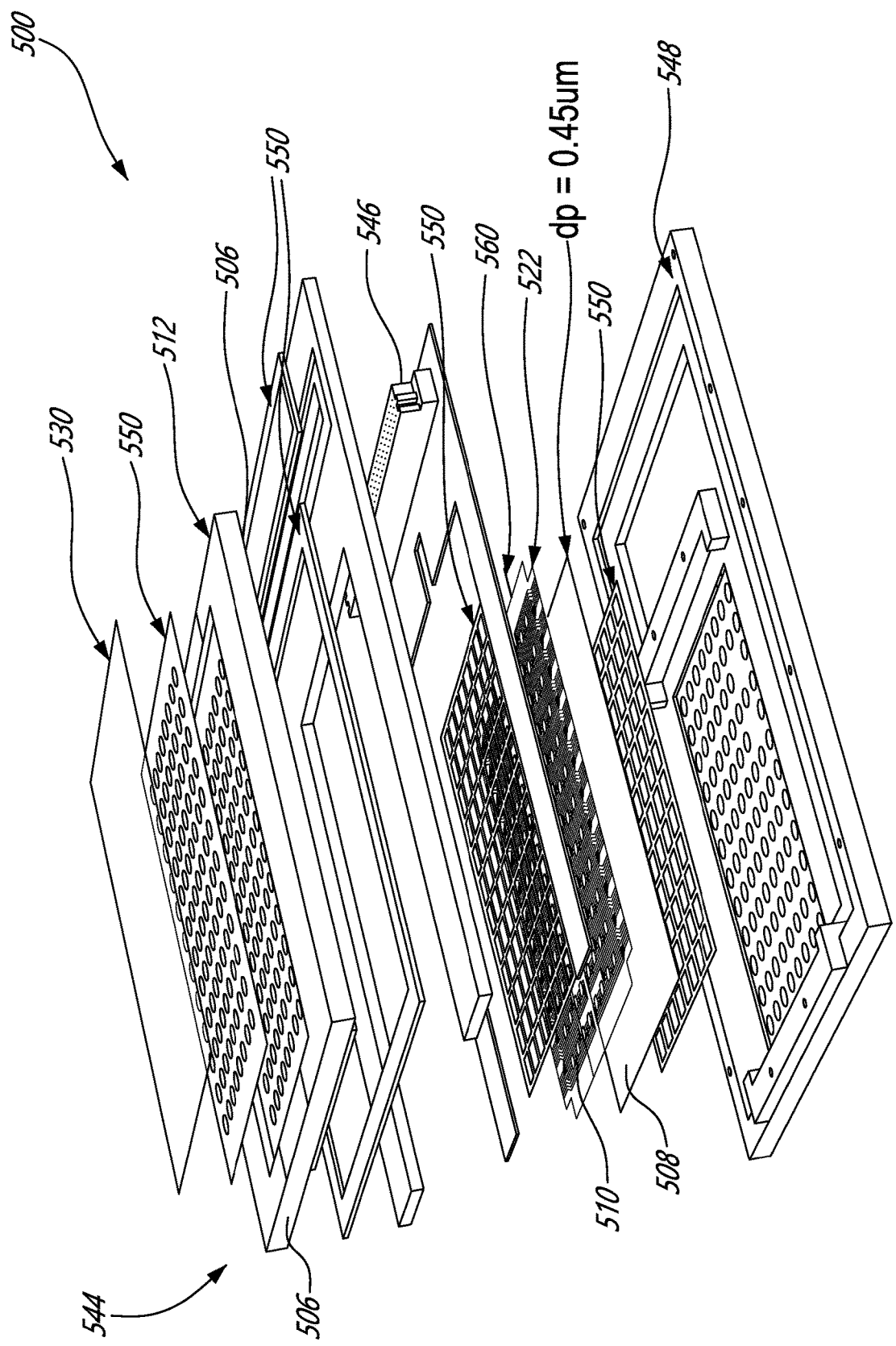
FIG. 5A is an exploded view of the cellular behaviour monitoring device, in accordance with one or more embodiments.

As illustrated in FIG. 5A, the layered structure 544 of the cellular behaviour monitoring device 500 has: a well plate 506 having a rectangular array of 96 wells 512, a filter membrane 508, an electrode layer 510 having gold-plated electrodes 522, a window 530 and O-rings 550 for hermetically sealing the parts to one another where necessary. The wells 512 are hermetically sealed from each other and from the external environment, except at the bottom, where the filter membrane 508 is installed. The window 530 of the cellular behaviour monitoring device 500 is made of plastic such as Plexiglas to let the daylight pass through to the wells

512. In this embodiment, the cellular behaviour monitoring device 500 has a bottom plate 548 having holes 549 aligned with the wells 512, as best shown in FIG. 5B. The bottom plate 548 has been fabricated using 3D printing with ABS and rubber material in this embodiment. However, the material and the fabrication method with which the bottom plate 548 is made can differ in some other embodiments.

The well plate 506 also has 96 wells 512 at the bottom allowing contact with the soil and the environment through the filter membrane 508 to provide the nutrients necessary for growth. An example of such the filter membrane 508 can include, but not limited to, the membrane Versapor 450 Acrylic Copolymer Membrane by Pall, which can have a thickness of about 80 μm and pore dimensions of about 0.1 to 0.22 μm. A modular approach is adopted to connect the layered structure 544 with the electronic board 542 through a dedicated connector 546 for providing full flexibility. The gold-plated electrode layer 510 is electrically connected with the connector 546 through a printed circuit board soldered with the array of 96 electrodes 522 using an anisotropic conductive tape 560. An interdigitated design (also referred to as "interspersed design") can be used for the electrodes 522 since this configuration provides a better sensitivity than a classic two electrodes system. This is caused by the multiple electrode pairs instead of the single one in a two-electrode configuration. Contact fingers are provided for all electrodes to enable an electric connection with the electronic circuit board. In this configuration, five contact fingers allow the interrogation of 4 wells (one line is common), there are 12 sets of 4 electrodes/wells on each side of the gold-plated electrode layer.

It is intended that the housing, the connectors (if any), the location of the electronic board relative to the well plate can differ from one embodiment to another. As such, the cellular behaviour monitoring device 500 can be fully customizable to be adapted to specific applications, as need may be.

Figure 6:
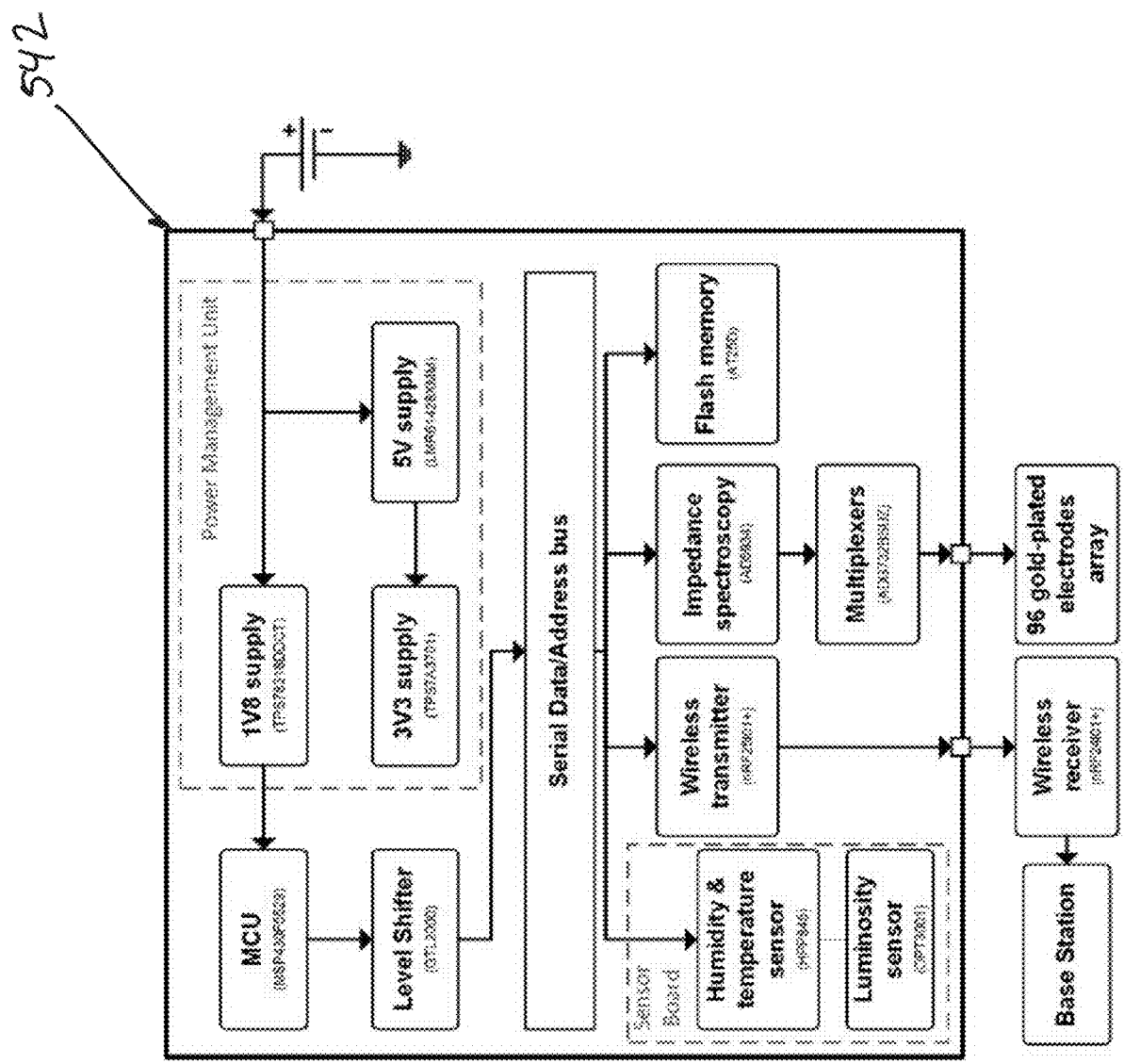
FIG. 6 is a schematic view of an example of the controller of FIG. 5, in accordance with one or more embodiments.

FIG. 6 shows an example block diagram of the electronic board 542. As depicted, the electronic board 542 has a 96-channel electro-chemical impedance (EIS) spectroscopy circuit to read the growth rate inside each well using an impedance electrodes array, a flash memory to store and accumulate the sensors data over a period of several months, a low-power micro-controller unit (MCU), a power management unit (PMU), and a low-power wireless transceiver to transmit the sensor data stored in flash memory to a base station, when a receiver is located within the transmitting range of the cellular behaviour monitoring device 500. Additional sensors are provided to measure various environmental parameters, such as luminosity, humidity, temperature, pH, and CO2, in order to monitor the growth conditions of the microorganisms inside the wells. The electronic board is controlled by a MSP430F5529 MCU from Texas Instrument. The MSP430F5529 MCU is an ultra-low-power microcontroller based on a 16-bit CPU which features multiple low-power modes of operation to further reduce power consumption by disabling various peripherals and internal clock signals. In this specific embodiment, which implements energy saving schemes to save as much power as possible and extends the autonomy of the cellular behaviour monitoring device 500 when placed in the field. It has two operating modes: 1) a read mode, in which all sensor measurements are performed sequentially, and 2) a sleep mode, in which all interface circuits and sensors remain idle to save energy between sensor measurements. Every five hours, a timer triggers an interruption bringing the MCU back in read mode and perform sensors measurements.

Using these power saving schemes, the cellular behaviour monitoring device 500 achieves an average power consumption of 140.4 mW and an idle mode power consumption of 81 μW, which represents less than 0.06% of the power consumption obtained in normal mode, leading to a greater battery life span. The microcontroller is operating on a low-frequency 8-MHz clock to limit power consumption in the MCU and other digital circuits. A UART port is accessible via a connector for debugging and through data harvesting when a wireless communication system is not available.

Power is provided to the cellular behaviour monitoring device 500 electronic board via a Tadiran TL5930F battery which as a temperature operating range of −55° C. to +85° C. This battery is rated at a nominal 3.6 V and is also equipped with a capacitor which is charged by the battery to provide a current boost when it is needed at start-up of the cellular behaviour monitoring device 500 in cold temperature. This 3.6 V voltage supply is stepped down to a 1.8-V supply for the MCU using an ultralow power low-dropout regulator (LDO) TPS78318 from Texas Instruments specifically selected to be as energy efficient as possible since it is required to be always enabled to supply the MCU. A LMR61428 from Texas Instruments step-up DC-DC switching regulator is used to step-up the 3.6-V supply into a 5-V supply. This 5-V voltage is then used to produce the 3.3V, which is used to supply all other components of the system, except the MCU. The 5-V supply also supplies the external soil humidity probe. When the cellular behaviour monitoring device 500 is in sleep mode, the MCU disables the 3.3-V supply to save power since all the building blocks supplied by this voltage are no longer required in sleep mode. A load switch controlled by the MCU is also implemented ahead of the regulators in order to completely cut the regulators supply when the cellular behaviour monitoring device 500 goes into sleep mode.

Battery voltage is monitored using one of the analog to digital converter inside the MCU via a voltage divider network. The voltage data is written in the memory along with the EIS and the environmental sensor data after each analysis performed every 5 hours. From the performance summarized in Table I, it is possible to estimate the battery lifetime. Since the device is waking up every 5 hours to run a complete analysis, we estimate that there will be around 5 analyses every day for a total of 13.33 minutes where the cellular behaviour monitoring device 500 is being the active mode every day. Since the cellular behaviour monitoring device 500 remains in sleep mode the rest of the time, where current consumption is greatly reduced, we can calculate a weighted average of the current consumption, and then estimate the battery lifetime. Doing so, we obtain a lifetime of 2019 days in ideal conditions. We can estimate that this duration can be cut by half to account for the effect of the cold temperature on the batteries, which gives an estimated lifetime of 1009 days in the field. Besides, monitoring the battery voltage inside the cellular behaviour monitoring device 500 allows to estimate the device lifetime and will later allow the implementation of advanced energy saving schemes that will adapt to temperature and/or to other varying environmental parameters.

The AD5934 digital signal processor provides the real and imaginary parts of the measured impedance. These values are calculated with a DFT (digital Fourier transform) performed by the AD5934 on 1024-point of the sampled signal. In order to achieve a good precision however, a calibration process is required. Because of this before every set of measurements the cellular behaviour monitoring device 500 measures the impedance of a known resistor selected from a calibration network of four resistors depending on the expected impedance range to be measured. The cellular behaviour monitoring device 500 is programmed to measure these impedance values, and to compare them with known values before running the EIS analysis on the wells. Resistors are used in the calibration process so that the measured phase ($\phi_{calib}$) is only due to the AD5934 internal circuits and is not influenced by additional components. The measured impedance values of the culture wells are then corrected by subtracting the phase $\phi_{calib}$ to the calculated phase value and then using the magnitude and phase to obtain the imaginary and real part of the impedance. The AD5934 is programmed to generate a 2-Vpp sinusoidal excitation signal, which is required to be scaled down not to harm the microorganisms found in the wells. Using an operational amplifier in inverting configuration it is reduced to a 5 mVpp signal and it is also re-centered at 1.65V using an AC coupling and a voltage divider. This signal is fed into a buffer and then an analog multiplexer can direct this signal to the calibration network or the next multiplexer layer to the wells. Three 1:32 analog multiplexers are used to sequentially dispatch the excitation to each of the 96 electrodes located inside the culture wells. The resistance of the signal path, from the AD5934 to the electrode, depends on the PCB trace length and on the multiplexers internal resistances. It has a measured average value of 8Ω in this design. Currently, this parasitic value is compensated manually in the MCU firmware of the cellular behaviour monitoring device 500, but this procedure can easily be automated in future versions. The measured impedance signal then gets amplified so it falls back into the reading range of the AD5934 to allow it to function as intended. When the cycle is completed for each of the 96 wells, data is sent to the MCU via an I2C bus to be saved in the on-board Flash memory. A 16 MHz crystal oscillator is supplied to the AD5934 to generate the various excitation frequencies. The time required to perform a complete EIS analysis of the 96 wells depends on the selected excitation frequency. The time of analysis decreases with the excitation frequency and as we use a higher frequency the capacitive part of the impedance becomes smaller relatively to the resistive part. Hence, this design uses an excitation frequency of 2 kHz to perform a complete analysis, which provides a good trade-off, and leads to a time of analysis of 2 minutes and 40 seconds. Since the cold temperature of the northern regions usually results into lower microorganism growth rates, a low sampling rate of 5 hours between each 96 well EIS measurement and other sensor measurement is used in this design. The cellular behaviour monitoring device 500 wakes up from idle mode every 5 hours and measures and stores all sensors data, and then falls back into sleep mode between sampling intervals to save energy.

Two sensor chips are used to monitor temperature, humidity and luminosity are mounted directly on the electronic board of the cellular behaviour monitoring device 500. The HPP845 temperature and humidity sensor from TE Connectivity, Switzerland is used for its low power consumption and its dual integration of both sensors in a small package. To measure ambient light, the OPT3001 from Texas Instruments, USA is selected since it allows the measurement of light across a wide range of luminosity, going from 0.01 lux to 83k lux, and presents low-power consumption. The light sensor can monitor the luminosity through a small transparent window installed in the housing of the main electronic board. Thus, the location of the sensor within the PCB falls directly under this window. Then, the measured environmental data is transmitted via an I2O bus to the MCU, and is then stored in the flash memory via a SPI bus, like EIS data. Environmental sensor measurements are performed every five hours, in conjunction with impedance measurements. $CO_2$ and pH sensors will also be added to the sensor interface in the near future.

Figure 7:
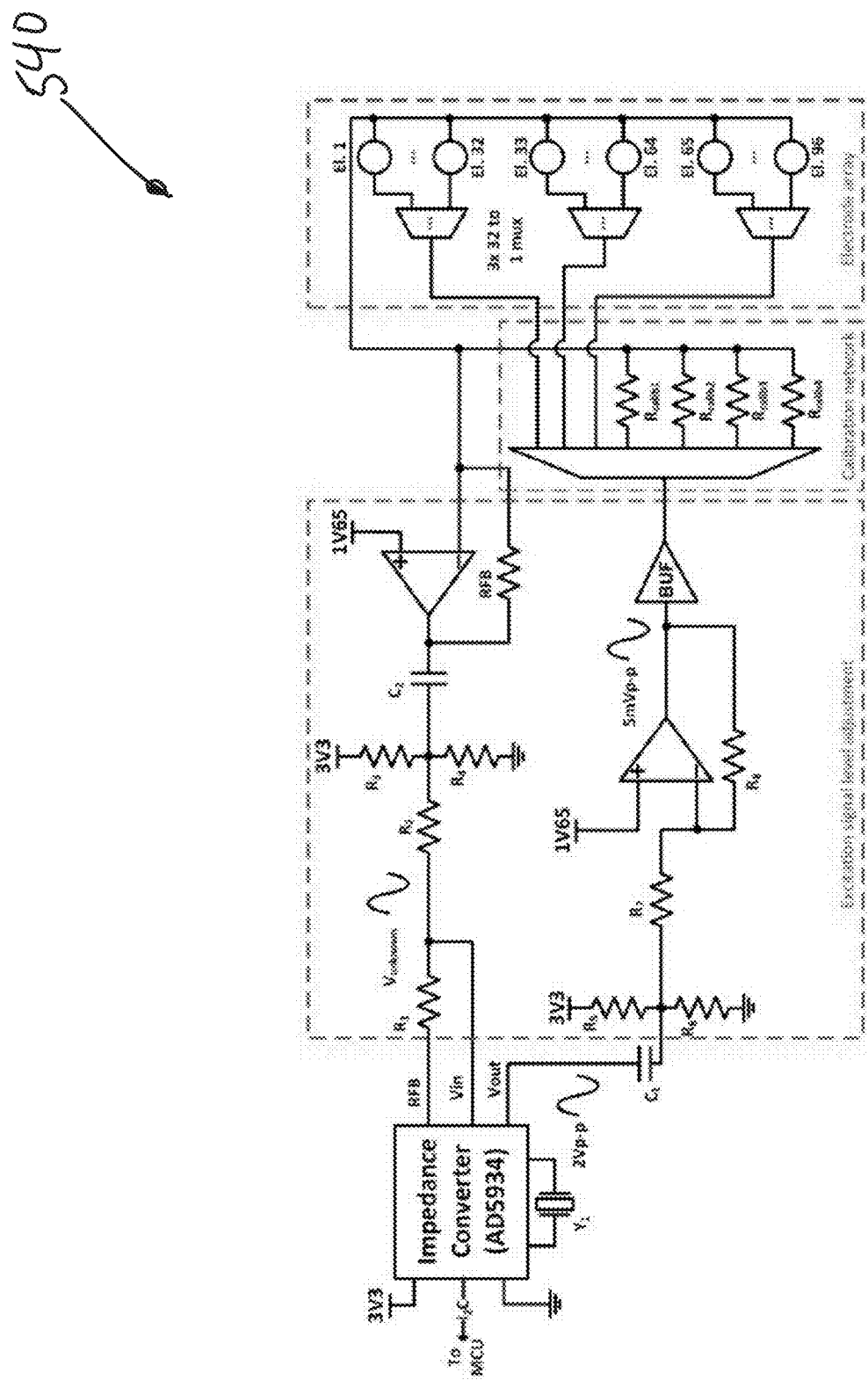
FIG. 7 is a schematic view of an example of the impedance monitoring system of FIG. 5, in accordance with one or more embodiments.

Impedance spectroscopy data of microorganisms growing inside the 96 wells of the cellular behaviour monitoring device 500 are measured using a dedicated multichannel circuit, the schematic of which is shown in FIG. 7. The multichannel circuit uses a AD5934 chip, from Analog Devices to perform impedance spectroscopy in this specific embodiment. The AD5934 chip is a 12-bit impedance converter, which can produce excitation signals across a wide range of frequencies to measure electro-chemical impedance using the gold-plated electrodes. This 12-bit impedance converter is frequently utilized in such systems since it is easy to use and interface with and also offers a good range of excitation frequencies that can go up to 100 kHz. Before any measurements are performed, the cellular behaviour monitoring device 500 goes through a calibration process to adjust its gain, with respect to the expected range of the impedance to be measured. For this purpose, the cellular behaviour monitoring device 500 can choose from four resistor values (Rcalib) that are mounted on the electronic board. The cellular behaviour monitoring device 500 is programmed to measure these impedance values, and comparing them to its known values before running the analysis on the wells. The AD5934 chip can produce a 2-Vpp excitation signal, which can be fed into an inverting amplifier, and decreased to 5 mVpp. This signal is also re-centered at 1.65 V using AC coupling and a voltage divider, and then goes through a buffer, and then through a multiplexer.

This multiplexer can either connect the signal to the calibration resistors, if the cellular behaviour monitoring device 500 is in a calibration phase, or to one of the three other 1:32 analog multiplexers, to dispatch the excitation signal to the right electrode, and measure the corresponding impedance, according to a time division multiplexing scheme (see FIG. 7). The impedance signal from the current electrode is then amplified to fall within a suitable range for the AD5934 chip to perform its analysis using a discrete Fourier transform. Once all 96 impedance readings are completed, data is sent to the MCU through an I2O bus, and is then written directly into the flash memory chip installed on the electronic board. The cold temperature of the Northern regions can allow for lower microorganism growth rates.

An interdigitated design is used for the electrodes since this configuration provides a better sensitivity than a classic two electrodes system. This is caused by the multiple electrode pairs instead of the single one in a two-electrode configuration. Contact fingers are provided for all electrodes to enable an electric connection with the electronic circuit board. In this configuration, five contact fingers allow the interrogation of 4 wells (one line is common), there are 12 sets of 4 electrodes/wells on each side of the gold-plated electrode layer.

Power is provided to the electronic board of the cellular behaviour monitoring device electronic 500 via a Tadiran TL5930F battery which as a temperature operating range of −55° C. to +85° C. This battery is rated at a nominal 3.6 V and is also equipped with a capacitor which is charged by the battery to provide a current boost when it is needed at start-up of the cellular behaviour monitoring device 500 in cold temperature. This 3.6 V voltage supply is stepped down to a 1.8-V supply for the MCU using an ultralow power low-dropout regulator (LDO) TPS78318 from Texas Instruments specifically selected to be as energy efficient as possible since it is required to be always enabled to supply the MCU. A LMR61428 from Texas Instruments step-up DC-DC switching regulator is used to step-up the 3.6-V supply into a 5-V supply. This 5-V voltage is then used to produce the 3.3V, which is used to supply all other components of the system, except the MCU. The 5-V supply also supplies the external soil humidity probe. When the cellular behaviour monitoring device 500 is in sleep mode, the MCU disables the 3.3-V supply to save power since all the building blocks supplied by this voltage are no longer required in sleep mode. A load switch controlled by the MCU is also implemented ahead of the regulators in order to completely cut the regulators supply when the cellular behaviour monitoring device 500 goes into sleep mode.

Battery voltage is monitored using one of the analog to digital converter inside the MCU via a voltage divider network. The voltage data is written in the memory along with the EIS and the environmental sensor data after each analysis performed every 5 hours. From the performance summarized in Table I, it is possible to estimate the battery lifetime. Since the device is waking up every 5 hours to run a complete analysis, we estimate that there will be around 5 analyses every day for a total of 13.33 minutes where the cellular behaviour monitoring device 500 is being the active mode every day. Since the cellular behaviour monitoring device 500 remains in sleep mode the rest of the time, where current consumption is greatly reduced, we can calculate a weighted average of the current consumption, and then estimate the battery lifetime. Doing so, we obtain a lifetime of 2019 days in ideal conditions. We can estimate that this duration can be cut by half to account for the effect of the cold temperature on the batteries, which gives an estimated lifetime of 1009 days in the field. Besides, monitoring the battery voltage inside the cellular behaviour monitoring device 500 allows to estimate the device lifetime and will later allow the implementation of advanced energy saving schemes that will adapt to temperature and/or to other varying environmental parameters.

The cellular behaviour monitoring device 500 is equipped with a 32 Mb on-board Flash memory chip AT25DF321A from Adesto Technologies to store the measured impedance and environmental data. For each impedance analysis performed, the impedance magnitude and phase are stored along with the corresponding well number, so each measured value can be associated with the right well when retrieving the data. At each analysis, the last address used in the memory along with the corresponding sample number is store in a dedicated page in order to keep track of the measurement data and timing, and not lose any measurement values in the event of an unexpected system reset. When the cellular behaviour monitoring device 500 exits sleep mode, it first reads this page, and then starts writing data from that point in the memory and so on. Long-term data storage and data integrity are critical in this application, especially when a wireless connection or a base station is not available to retrieve the data. In this case, the data can be retrieved through a UART to USB converter that is installed on the board to transfer the data from the flash memory to a computer user interface, and save it into a csv file.

Hence, the cellular behaviour monitoring device 500 gets into the reading mode for a short period of time every five hours to make 96 impedance measurements, and falls back to sleep mode between measurements to conserve energy.

Sensors used to monitor temperature, humidity and luminosity are installed on a separate sensor board that connects to the main electronic board through a dedicated connector. A small transparent window is opened in the housing of the main electronic board to monitor the luminosity. Thus, the sensor board is placed directly under this window. The measured environmental data is transmitted via an 120 bus to the main electronic board and the MCU, and stored in flash memory. Environmental sensor measurements are performed every five hours, in conjunction with impedance measurements.

To simplify the data recovery process, wireless communication is implemented inside the cellular behaviour monitoring device 500 using, for instance, an nRF24l01+ wireless transceiver from Nordic Semiconductor and an external antenna. The cellular behaviour monitoring device 500 is communicating in the 2.4-GHz ISM band and provides a data rate of 1 Mbps in this embodiment. During experiments that were performed in the field, the cellular behaviour monitoring device 500 could transmit data directly to a base station equipped with a receiver placed inside a nearby cabin. Wireless communications are convenient in this application since the cellular behaviour monitoring device 500 is likely to be covered in snow or moved from its original location in further studies. In such cases, the wireless connection can be used to located and to wake up the cellular behaviour monitoring device 500, and to transmit the data stored in memory to a8anearby receiver module.

Figure 8C:
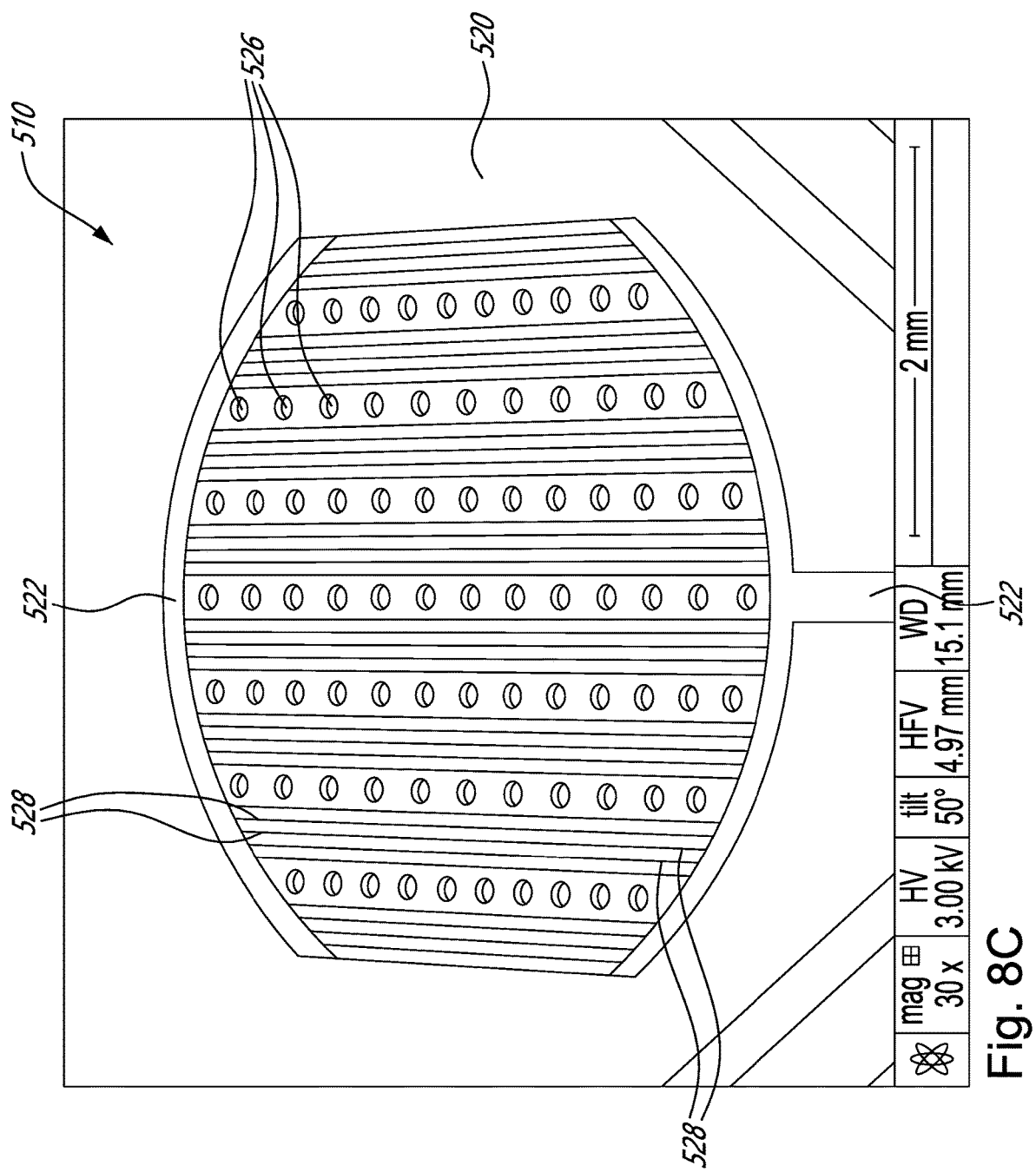
FIG. 8C is an enlarged view of the electrode layer of FIG. 8A or 8B, in accordance with one or more embodiments.

The impedance electrodes 522 of the electrode layer 510 such as those shown in FIGS. 8A, 8B and 8C can be fabricated in two steps. First, a layer of gold is deposited on a sheet of polyimide in a vacuum chamber. Then, the electrodes are engraved with a laser to form 96 individual electrodes such as those shown in FIG. 8A. Electrodes 522 are drawn into a two-comb shape layout such as shown in FIGS. 8B and 8C, where apertures 526 are made between monitoring fingers 528 with the laser for providing contact with the soil and the environment at the bottom of the cellular behaviour monitoring device 500. As shown in this example, the apertures 526 of the electrode layer 510 are away from the monitoring fingers 528 through the substrate 520. Copper lines with pads are provided for all electrodes to enable an electric connection with the electronic circuit board. Since five copper lines allow to interrogate electrodes for 4 wells, there can be 12 sets of 4 electrodes/wells on each side of the gold-plated electrode layer.

Power can be provided to the electronic board of the cellular behaviour monitoring device 500 via a set of six CR123 lithium batteries, in this example. They are disposed in two groups connected in parallel, each including three batteries connected in series. The 9 V voltage supply is stepped down to a 1.8 V supply for the MCU. A second step-down converter is used to convert the 9 V supply into 3.3 V supply, which is used to supply all other parts of the cellular behaviour monitoring device 500, except the MCU. When the cellular behaviour monitoring device 500 is in the sleep mode, the MCU may disable the 3.3 V supply to save power. A 5 V supply is also implemented in the cellular behaviour monitoring device 500 to power an external soil humidity probe that may be added to the cellular behaviour monitoring device 500 in some embodiments. The 9 V supply accommodates thermal de-rating of batteries. Different power schemes may be employed using low temperature battery chemistries in some other embodiments.

The cellular behaviour monitoring device 500 of this example was fully characterized and tested in the laboratory, and was used to perform bacteria growth measurement in-vitro in an incubator. Moreover, sensor data and DNA sequencing results are presented following a pilot study performed with the cellular behaviour monitoring device 500 in the village of Kuujjuarapik, in Northern Canada.

Figure 9B:
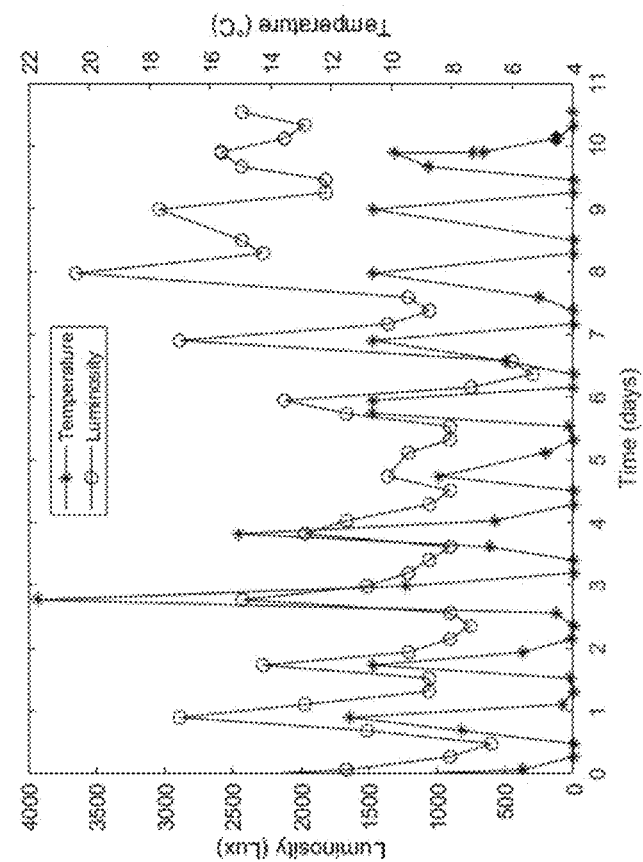
FIG. 9B is a graph showing luminosity as function of elapsed time, showing luminosity values measured using the cellular behaviour monitoring device of FIG. 5 over time.
Figure 9A:
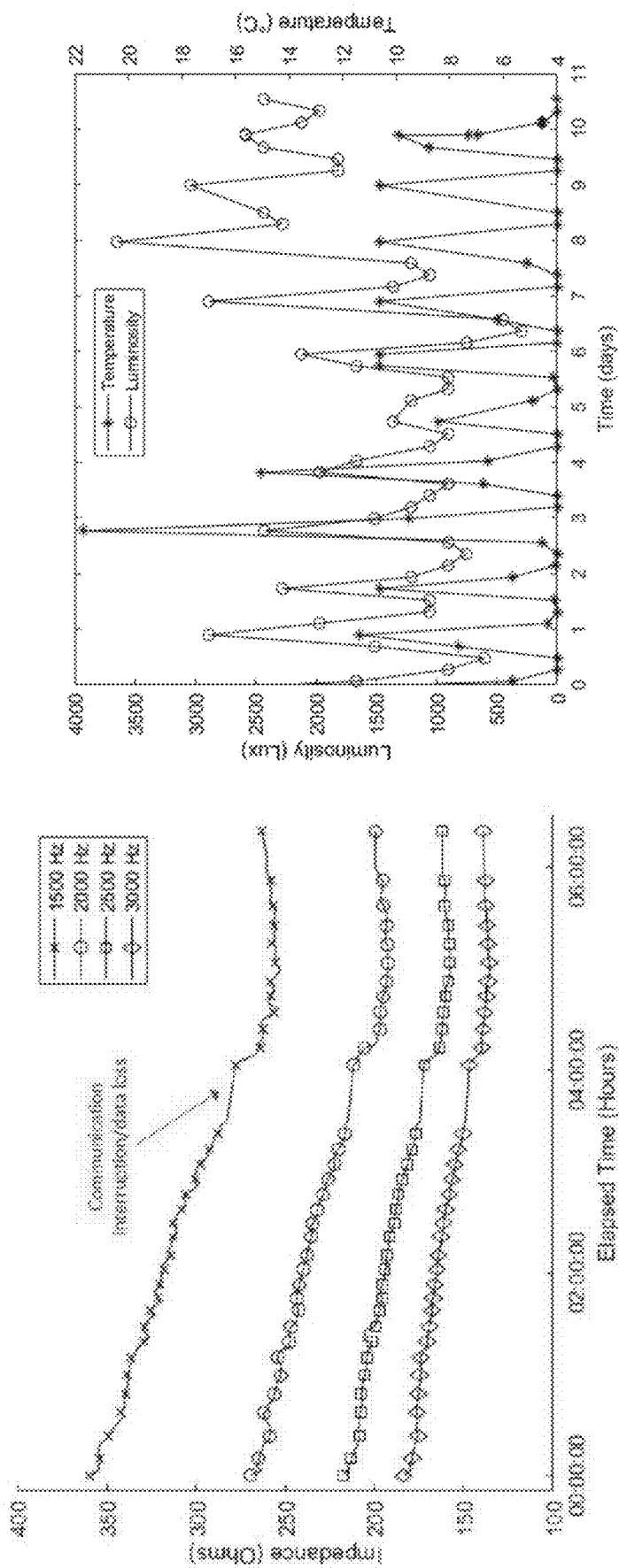
FIG. 9A is a graph showing impedance as function of elapsed time, showing impedance values measured using the cellular behaviour monitoring device of FIG. 5 over time.

More specifically, the cellular behaviour monitoring device 500 was tested in the laboratory, inside an incubator with a known bacterial strain. Wells were filled with *Escherichia coli* B (HER1024) obtained from the Félix d'Hérelle Reference Center for Bacterial Viruses at Université Laval. *E. coli* was grown overnight in Trypticase soy broth (TSB) with agitation at 37° C. Strain was diluted in TSB to approximately 1×106 cfu/ml and 100 µl of the dilution was put in 6 wells of the 96-wells plate. Impedance measurements are reported in FIG. 9A and analyzed for one well. The plate was incubated at 37° C. without agitation and read for a period of about six and half hours. The cellular behaviour monitoring device 500 was configured to perform a sweep of the excitation frequency on a range going from 1 kHz to 4 kHz such that the capacitance can represent the major part of the measured impedance shown in FIG. 9A. The decrease in the impedance seen in FIG. 9A represents a growth of the population of microorganisms in the wells.

The pilot study with the cellular behaviour monitoring device 500 was performed at a latitude of 55 degrees in the village of Kuujjuarapik, Nord-du-Québec. Soil samples were diluted one million-fold with TSB culture media and put into the wells of the cellular behaviour monitoring device 500. The diluted solution was sealed between semi-permeable membranes in the cellular behaviour monitoring device 500 and installed in contact with the soil to provide the nutrients necessary for growth. The cellular behaviour monitoring device 500 was installed and incubated in its environment for 10 days. The temperature and the luminosity were simultaneously measured 5 times a day during this period (see FIG. 9B).

Back in the laboratory, one well was swabbed to collect microbes and bacterial DNA was extracted from the sample. The DNA sequencing results shown 55.29% of *Pseudomonas* sp UK4, 36.989% of *Pseudomonas* unclassified, 3.76% of *Curtobacterium* unclassified, 1.64% of *Providencia* unclassified, 1.21% of *Providencia burhodogranariea*, 0.59% of *Pseudomonas fragi*, 0.39% of *Sphingobacterium* unclassified, 0.13% of *Stenotrophomonas maltophilia*. Sequencing libraries were prepared using the Nextera XT protocol and sequencing of the metagenome with paired-end 250 nucleotides reads was performed on the Illumina MiSeq system. Metagenomes were assembled using Ray Meta and taxonomical origin of the assembled contigs was determined using Ray Meta. Total assembly size was 42.6 million nucleotides. Overall, 21 million assembled nucleotides were potentially originating from *Pseudomonas* bacteria, indicating that at least three strains or species of *Pseudomonas* were present in the sample, since their genome size is usually between 5.5 and 7 million nucleotides.

In this example, there is described an example of a cellular behaviour monitoring device 500 system allowing for the in-situ culture of microorganisms and monitoring of their growth in the field. The cellular behaviour monitoring device 500 can be used to measure the impacts of climate changes and global warming on the Northern region microbiome, for instance. The cellular behaviour monitoring device 500 uses impedance spectroscopy to measure the growth rate of the microorganisms inside 96 wells. Several other sensors are provided for environmental monitoring. Impedance and environmental data are saved on-board in flash memory, and transmitted to a base station through a wireless connection. Field measurements were performed and confirmed that microorganisms can be grown inside the wells of the cellular behaviour monitoring device 500 in the field. In next steps, the multilayer design of the cellular behaviour monitoring device 500 may allow to apply selective conditions in the middle layer were the single strain microorganism growth occurs by providing culture media with different pH alternatives. Even contaminants such as heavy metals could be added to the upper layer, enabling additional selection pressures for microorganisms. Additionally, the cellular behaviour monitoring device 500 will be used to identify, and characterize viruses associated with the microorganisms isolated within the wells.

The cellular behaviour monitoring device 500 may be configured to identify, extract, assemble and/or annotate viral and bacterial sequence data, as well as experiments with keystone host-virus systems of particular interest for several areas, such as medicine and pharmacology.

FIGS. 10A and 10B show another example of a cellular behaviour monitoring device 600 for monitoring changes in behaviour of cells contained in a sample. As best shown in FIG. 10B, the cellular behaviour monitoring device 600 has a well plate 606 which has a first surface 606*a*, and a second surface 606*b* opposite to the first surface 606*a*. The well plate 606 also has sample receiving wells 612 recessed from the first surface 606*a* of the well plate 606. The cellular behaviour monitoring device 600 has a filter membrane 608 extending across the first surface 606*a* of the well plate 606. As shown, the filter membrane 608 hermetically covers the sample receiving wells 612. The filter membrane 608 has pores extending through the filter membrane 608 which are both nutrient-permeable and cell-impermeable, as discussed above. The cellular behaviour monitoring device 600 has an electrode layer 610 extending across the filter membrane 608. The electrode layer has a substrate 620 and behaviour monitoring electrodes 622 spaced-apart from one another in a region of the substrate 620. The electrode layer 610 has nutrient-permeable apertures distributed across the region. The apertures can extend across the substrate 620, across the behaviour monitoring electrodes 622, or both. As shown, the sample receiving wells 612 are provided with respective growth medium 670 to help the cells of the samples grow over time. In some embodiments, the growth medium 670 are of similar type in all the sample receiving wells 612. However, in some other embodiments, the growth medium are different from one receiving well 612 to another. In bioremediation applications, the growth medium 670 can be designed to select one or more contaminants. In this way, the cellular behaviour monitoring device 600 can monitor at which rates the cells of the sample receiving wells 612 grow and then draw conclusions based on the type, the volume and/or the selected contaminant associated to the growth medium 670 in corresponding ones of the particular sample receiving wells 612, for instance.

In this specific embodiment, the cellular behaviour monitoring device 600 has an impedance monitoring system 640 connected to the behaviour monitoring electrodes 622. The impedance monitoring system 640 measures impedance values indicative of impedance between the behaviour monitoring electrodes 622 over time as the cells within the sample receiving wells 612 grow. The cellular behaviour monitoring device 600 has a controller 642 communicatively coupled to the impedance monitoring system 640 in this embodiment. The controller 642 generates a wireless signal based on the measured impedance values towards a remotely located wireless receiving base (not shown). In this specific embodiment, the impedance monitoring system 640 and the controller 642 are part of a printed-circuit board which extends in a manner coplanar to the electrode layer 610. The impedance monitoring system 640 and the controller 642, and any components of the printed-circuit board, are powered using a battery or battery pack 672.

As best shown in FIG. 10A, the cellular behaviour monitoring device 600 has a housing 674 hermetically enclosing the well plate 606, the electrode layer 610, and all the other components of the cellular behaviour monitoring device 600. The housing 674 includes a bottom plate 674a and a lid 674b which is removably mounted to the bottom plate 674a. As shown, the lid 674b has an optically transparent window 630 allowing sunlight to reach the sample receiving wells 612. As shown in FIG. 10B, the bottom plate 674a has openings 676 aligned with the sample receiving well 612 to allow fluid communication therebetween.

Figure 11:
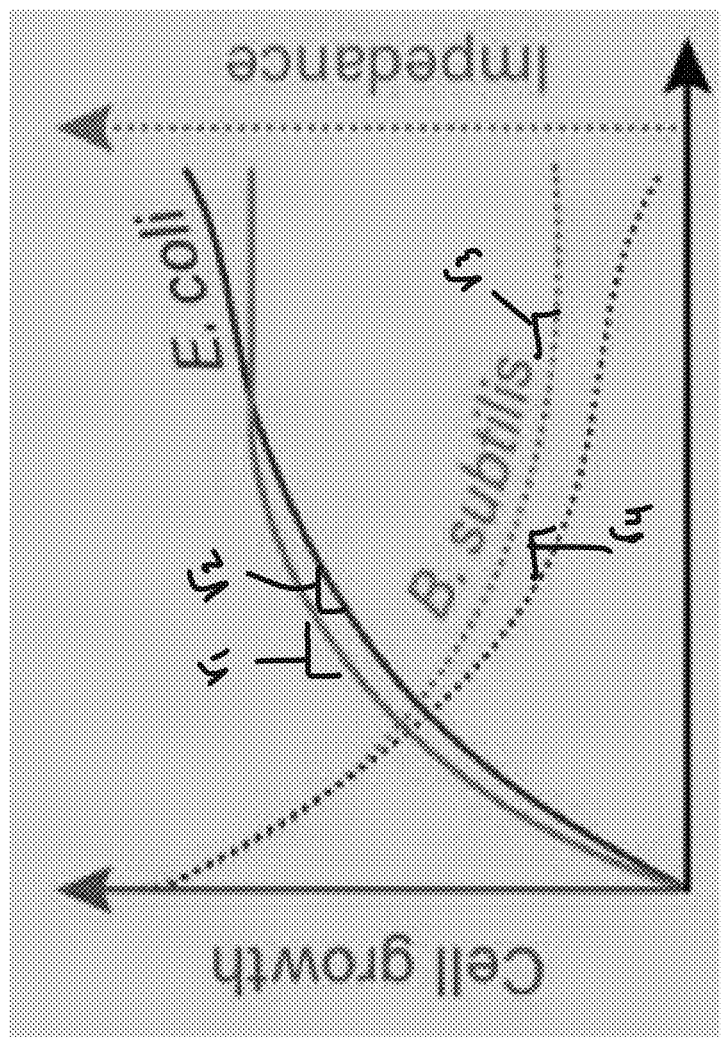
FIG. 11 is a graph showing cell growth and impedance varying over time, in accordance with one or more embodiments.

FIG. 11 shows a graph of cell growth and impedance as function of time for four different sample receiving wells 612. As shown, the controller 642 can, based on the impedance values measured by the impedance monitoring system 640, determine growth rates, e.g., growth rates $r_1$, $r_2$, $r_3$ and $r_4$, indicating at which rate the cells within each of the sample receiving wells 612 grow. The controller 642 can be configured to store the impedance values and/or the growth rates on a given memory (e.g., a flash memory), and/or to transmit the impedance values and/or the growth rates to a remote base station. The As can be understood, the examples described above and illustrated are intended to be exemplary only. For instance, the surrounding environment in which the cellular behaviour monitoring device is positioned can include, but not limited to, ground such as the one found in Northern environments, underground, underwater and the like. It is encompassed that the cellular behaviour monitoring device can be used for research purposes, industrial applications such as in the mining industry and/or in the decontamination industry, for instance. The scope is indicated by the appended claims.

What is claimed is:

1. A cellular behaviour monitoring device for monitoring changes in behaviour of cells contained in a sample, the cellular behaviour monitoring device comprising:
    a well plate having a first surface, a second surface opposite to the first surface, and at least one sample receiving well recessed from the first surface of the well plate;
    a filter membrane extending across the first surface of the well plate and covering the at least one sample receiving well, the filter membrane having a plurality of pores extending through the filter membrane, the plurality of pores having a dimension exceeding a nutrient dimension and being smaller than a cell dimension; and
    an electrode layer extending across the filter membrane, the electrode layer having a substrate and a plurality of behaviour monitoring electrodes spaced-apart from one another in a region of the substrate, the region being aligned with the at least one sample receiving well, the electrode layer having a plurality of apertures distributed across the region, the plurality of apertures having a dimension exceeding the dimension of the plurality of pores, at least some of the plurality of pores being aligned with at least some of the plurality of apertures to allow fluid communication therebetween.

2. The cellular behaviour monitoring device of claim 1 wherein the plurality of behaviour monitoring electrodes comprise at least a ground electrode and a well electrode, the ground electrode having a plurality of monitoring fingers extending across the region, the ground electrode having a plurality of monitoring fingers extending across the region and being spaced-apart and interspersed with the plurality of monitoring fingers of the ground electrode.

3. The cellular behaviour monitoring device of claim 1 wherein the electrode layer extends parallel to the filter membrane, the filter membrane being sandwiched between the well plate and the electrode layer.

4. The cellular behaviour monitoring device of claim 1 wherein the apertures of the electrode layer are spaced-apart from the behaviour monitoring electrodes.

5. The cellular behaviour monitoring device of claim 1 wherein the at least one sample receiving well extends through the well plate between the first surface and the second surface.

6. The cellular behaviour monitoring device of claim 5 the cellular behaviour monitoring device further comprising an optically transparent lid extending across the second surface of the well plate, the optically transparent lid being transparent to sunlight.

7. The cellular behaviour monitoring device of claim 1 wherein the at least one sample receiving well extends partially through the well plate.

8. The cellular behaviour monitoring device of claim 1 further comprising an impedance monitoring system connected to the plurality of behaviour monitoring electrodes, the impedance monitoring system measuring a plurality of impedance values indicative of impedance between the behaviour monitoring electrodes over time.

9. The cellular behaviour monitoring device of claim 8 further comprising a controller communicatively coupled to the impedance monitoring system, the controller generating a signal based on the plurality of measured impedance values.

10. The cellular behaviour monitoring device of claim 9 wherein the controller determines a growth rate associated to the sample received in the at least one sample receiving well based on said signal.

11. The cellular behaviour monitoring device of claim 1 wherein the at least one sample receiving well of the well plate comprises a plurality of sample receiving wells being spaced-apart from one another on the first surface of the well plate.

12. The cellular behaviour monitoring device of claim 11 wherein the filter membrane and the electrode layer extending across the plurality of sample receiving wells.

13. The cellular behaviour monitoring device of claim 1 further comprising one or more growth medium within the at least one sample receiving well.

14. A method for monitoring changes in behaviour of a plurality of cell samples received in a plurality of sample receiving wells using a cellular behaviour monitoring device, the method comprising:
    covering the plurality of sample receiving wells with a filter membrane having a plurality of nutrient-permeable and cell-impermeable pores and with an electrode layer having a plurality of behaviour monitoring electrodes extending across said plurality of sample receiving wells, the electrode layer having at least some apertures aligned with at least some of the nutrient-permeable and cell-impermeable pores of the filter membrane to allow fluid communication therebetween; and
    the plurality of cell samples exchanging nutrients with a surrounding environment through the nutrient-permeable and cell-impermeable pores of the filter membrane and through the apertures of the electrode layer.

15. The method of claim 14 further comprising, using an impedance monitoring system connected to the plurality of behaviour monitoring electrodes, measuring a plurality of impedance values over time, the impedance values being indicative of impedance across the behaviour monitoring electrodes as cells of the plurality of cell samples grow over time.

16. The method of claim 15 further comprising, using a controller communicatively coupled to the impedance monitoring system, generating a signal based on said plurality of measured impedance values.

17. The method of claim 16 further comprising, using the controller, determining a plurality of growth rates associated to the cells sample received in the plurality of sample receiving wells based on said signal.

* * * * *